US010287338B2

(12) United States Patent
Nersissian et al.

(10) Patent No.: US 10,287,338 B2
(45) Date of Patent: May 14, 2019

(54) FACTOR VIII PROTEIN COMPOSITIONS AND METHODS OF TREATING OF HEMOPHILIA A

(71) Applicant: Miran Nersissian, Santa Monica, CA (US)

(72) Inventors: Aram M. Nersissian, Santa Monica, CA (US); Miran Nersissian, Santa Monica, CA (US)

(*) Notice: Subject to any disclaimer, the term of this patent is extended or adjusted under 35 U.S.C. 154(b) by 0 days.

(21) Appl. No.: 15/736,718

(22) PCT Filed: Jul. 7, 2016

(86) PCT No.: PCT/US2016/041399
§ 371 (c)(1),
(2) Date: Dec. 14, 2017

(87) PCT Pub. No.: WO2017/011275
PCT Pub. Date: Jan. 19, 2017

(65) Prior Publication Data
US 2018/0186857 A1 Jul. 5, 2018

Related U.S. Application Data

(60) Provisional application No. 62/191,211, filed on Jul. 10, 2015.

(51) Int. Cl.
A61K 9/00 (2006.01)
A61P 7/04 (2006.01)
A61K 38/00 (2006.01)
C07K 16/36 (2006.01)
C07K 14/755 (2006.01)

(52) U.S. Cl.
CPC .......... *C07K 14/755* (2013.01); *A61K 9/0026* (2013.01); *A61P 7/04* (2018.01); *C07K 16/36* (2013.01); *A61K 38/00* (2013.01)

(58) Field of Classification Search
CPC ......... A61K 38/00; A61K 9/0026; A61P 7/04; C07K 14/755; C07K 16/36
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis et al. |
| 4,704,692 A | 11/1987 | Ladner |
| 4,754,065 A | 6/1988 | Levenson et al. |
| 4,800,159 A | 1/1989 | Mullis et al. |
| 4,812,405 A | 3/1989 | Lair et al. |
| 4,816,567 A | 3/1989 | Cabilly et al. |
| 4,818,700 A | 4/1989 | Cregg et al. |
| 4,873,316 A | 10/1989 | Meade et al. |
| 4,929,555 A | 5/1990 | Cregg et al. |
| 5,225,539 A | 7/1993 | Winter |
| 5,304,489 A | 4/1994 | Rosen |
| 5,440,013 A | 8/1995 | Kahn |
| 5,530,101 A | 6/1996 | Queen et al. |
| 5,565,362 A | 10/1996 | Rosen |
| 5,585,089 A | 12/1996 | Queen et al. |
| 5,627,052 A | 5/1997 | Schrader |
| 5,670,153 A | 9/1997 | Weiner et al. |
| 5,686,073 A | 11/1997 | Campbell et al. |
| 5,693,762 A | 12/1997 | Queen et al. |
| 5,714,352 A | 2/1998 | Jakobovits |
| 5,723,323 A | 3/1998 | Kauffman et al. |
| 5,736,383 A | 4/1998 | Raymond |
| 5,763,192 A | 6/1998 | Kauffman et al. |
| 5,766,886 A | 6/1998 | Studnicka et al. |
| 5,814,476 A | 9/1998 | Kauffman et al. |
| 5,817,483 A | 10/1998 | Kauffman et al. |
| 5,824,514 A | 10/1998 | Kauffman et al. |
| 5,827,690 A | 10/1998 | Meade et al. |
| 5,837,249 A | 11/1998 | Heber-Katz et al. |
| 5,849,992 A | 12/1998 | Meade et al. |
| 5,888,768 A | 3/1999 | Raymond |
| 5,955,349 A | 9/1999 | Raymond |
| 5,976,862 A | 11/1999 | Kauffman et al. |
| 5,994,616 A | 11/1999 | Rosen |
| 6,075,181 A | 6/2000 | Kucherlapati et al. |
| 6,180,370 B1 | 1/2001 | Queen et al. |
| 6,204,023 B1 | 3/2001 | Robinson et al. |
| 6,258,559 B1 | 7/2001 | Zamost |
| 6,322,788 B1 | 11/2001 | Kim |
| 6,602,684 B1 | 8/2003 | Umana et al. |
| 6,632,926 B1 | 10/2003 | Chen et al. |
| 6,656,746 B2 | 12/2003 | Sprecher et al. |
| 6,709,659 B1 | 3/2004 | Lok et al. |
| 6,797,492 B2 | 9/2004 | Daugherty et al. |
| 7,060,800 B2 | 6/2006 | Gorman |

(Continued)

FOREIGN PATENT DOCUMENTS

| | | |
|---|---|---|
| EP | 404097 | 12/1990 |
| EP | 519596 | 12/1992 |

(Continued)

OTHER PUBLICATIONS

Adachi & Hasegawa, "Model of Amino Acid Substitution in Proteins Encoded by Mitochondrial DNA", J. Mol. Evol., 1996, 42:459-468.
Arbones et al., "Lymphocyte Homing and Leukocyte Rolling and Migration Are Impaired in L-Selectin-Deficient Mice", Immunity, 1994, 1(4):247-260.
Babcook et al., "A novel strategy for generating monoclonal antibodies from single, isolated lymphocytes producing antibodies of defined specificities", Proc. Natl. Acad. Sci. USA, 1996, 93:7843-7848.
Chang et al., "Inhibition of HIV infectivity by a natural human isolate of Lactobacillus jensenii engineered to express functional two-domain CD4", PNAS, 2003, 100(20):11672-11677.
Conrad et al., "Compartment-specific accumulation of recombinant immunoglobulins in plant cells: an essential tool for antibody production and immunomodulation of physiological functions and pathogen activity", Plant Mol. Biol., 1998, 38:101-109.

(Continued)

Primary Examiner — Marcela M Cordero Garcia
(74) Attorney, Agent, or Firm — Foley & Lardner LLP

(57) ABSTRACT

Compositions of recombinant FVIII protein comprising point mutations. Methods for using recombinant FVIII to activate FX and FIXa in cells and treat diseases mediated by the degradation of FVIII are described.

17 Claims, No Drawings

(56) References Cited

U.S. PATENT DOCUMENTS

| | | | |
|---|---|---|---|
| 7,119,179 | B1 | 10/2006 | Huynh et al. |
| 7,279,559 | B2 | 10/2007 | Jacobs et al. |
| 2013/0085110 | A1 | 4/2013 | Fay et al. |
| 2013/0184216 | A1 | 7/2013 | Besman et al. |
| 2014/0120071 | A1 | 5/2014 | Fay et al. |

FOREIGN PATENT DOCUMENTS

| | | |
|---|---|---|
| WO | WO-93/11161 | 6/1993 |
| WO | WO-95/00655 | 1/1995 |
| WO | WO-95/11984 | 5/1995 |
| WO | WO-95/27071 | 10/1995 |
| WO | WO-03/035691 A1 | 5/2003 |
| WO | WO-2013/123457 | 8/2013 |

OTHER PUBLICATIONS

Cramer et al., "Transgenic plants for therapeutic proteins: linking upstream and downstream strategies", Curr. Top. Microbol. Immunol., 1999, 240:95-118.
Dahoff et al., Atlas of Protein Sequence and Structure, 1978, 5(2):D345-D352.
Dharanipragada et al., "Synthetic linear and cyclic glucagon antagonists", Int. J. Pep. Protein Res., 1993, 42(1):68-77.
Dharanipragada et al., "The Absolute Configuration of an Intermediate in the Asymmetric Synthesis of Unusual Amino Acids", Acta. Crystallogr. C., 1992, C48:1239-1241.
Dimaio et al., "Synthesis of Chiral Piperazin-2-ones as Model Peptidomimetics", J. Chem. Soc. Perkin Trans., 1989, 1(9):1687-1689.
Eren et al., "Human monoclonal antibodies specific to hepatitis B virus generated in a human/mouse radiation chimera: the Trimera system", Immunol., 1998, 93:154-161.
Gallo et al., "The human immunoglobulin loci introduced into mice: V (D) and J gene segment usage similar to that of adult humans", European J. of Immun., 2000, 30:534-540.
Giomarelli et al., "Recombinant production of anti-HIV protein, griffithsin, by auto-induction in a fermentor culture", Protein Expression and Purification, 2006, 47:194-202.
Gonnet et al., "Exhaustive Matching of the Entire Protein Sequence Database", Science, 1992, 256:1443-1145.
Granados et al., "A New Insect Cell Line from Trichoplusia ni (BTI-Tn-5B1-4) Susceptible to Trichoplusia ni Single Enveloped Nuclear Polyhedrosis Virus", Journal of Invertebrate Pathology, 1994, 64(3):260-266.
Gray et al., "Secretion capture and report web: use of affinity derivatized agarose microdroplets for the selection of hybridoma cells", Journal of Immunological Methods, 1995, 182:155-163.
Green & Jakobovits, "Regulation of B Cell Development of Variable Gene Complexity in Mice Reconstituted with Human Immunoglobulin Yeast Artificial Chromosomes", J. Exp. Med., 1998, 188(3):483-495.
Green, L.L., "Antibody engineering via genetic engineering of the mouse: XenoMouse strains are a vehicle for the facile generation of therapeutic human monoclonal antibodies", J. of Immun. Methods, 1999, 231:11-23.
Hanes & Pluckthun, "In vitro selection and evolution of functional proteins by using ribosome display", Proc. Natl. Acad. Sci. USA, 1997, 94:4937-4942.
Hanes et al., "Ribosome display efficiently selects and evolves high-affinity antibodies in vitro from immune libraries", Proc. Natl. Acad. Sci. USA, 1998, 95:14130-14135.
Henikoff & Henikoff, "Amino acid substitution matrices from protein blocks", Proc. Natl. Acad. Sci. USA, 1992, 89:10915-10919.
Herlyn et al., "Anti-Idiotypic Antibodies Bear the Internal Image of a Human Tumor Antigen", Science, 1986, 232:100.
Hermonat & Muzyczka, "Use of adeno-associated virus as a mammalian DNA cloning vector Transduction of neomycin resistance into mammalian tissue culture cells", Proc. Natl. Acad. Sci. USA, 1984, 81:6466-6470.
Hollinger et al., "'Diabodies': Small bivalent and bispecific antibody fragments", Proc. Natl. Acad. Sci. USA, 1993, 90:6444-6448.
Homer and Yadava, "Some observations on the stereospecificity of weakly bound complexes of organic molecules", Tetrahedron Lett. 1988, 29:3853-3855.
Hood et al., "Molecular Farming of Industrial Proteins From Transgenic Maize", Adv. Exp. Med. Biol., 1999, 464:127-147.
Hruby et al., "Emerging approaches in the molecular design of receptor-selective peptide ligands: conformational, topographical and dynamic considerations", Biochem J., 1990, 268:249-262.
Hruby, V.J., "Minireview. Conformational Restrictions of Biologically Active Peptides Via Amino Acid Side Chain Groups", Life Sciences, 1982, 31(3):189-199.
Jakobovits et al., "Analysis of homozygous mutant chimeric mice: Deletion of the immunoglobulin heavy-chain joining region blocks B-cell development and antibody production", Proc. Natl. Acad. Sci. USA, 1993, 90(6):2551-2555.
Jakobovits et al., "Germ-line transmission and expression of a human-derived yeast artificial chromosome", Nature, 1993, 362(6417):255-258.
Jakobovits, A., "Humanizing the mouse genome", Current Biology, 1994, 4(8):761-763.
Jakobovits, A., "Production and selection of antigen-specific fully human monoclonal antibodies from mice engineered with human Ig loci", Advanced Drug Delivery Reviews, 1998, 31:33-42.
Jakobovits, A., "Production of fully human antibodies by transgenic mice", Current Opinion in Biotechnology, 1995, 6(5):561-566.
Jakobovits, A., "The long-awaited magic bullets: therapeutic human monoclonal antibodies from transgenic mice", Exp. Opin. Invest. Drugs, 1998, 7(4):607-614.
Jones et al., "The rapid generation of mutation data matrices from protein sequences", Comput. Appl. Biosci., 1992, 8(3):275-282.
Kahn et al., "The Incorporation of B-Turn Prosthetic Unites into Merrifield Solid Phase Peptide Synthesis", Tetrahedron Lett., 1989, 30(18):2317-2320.
Kazmierski & Hruby, "Asymmetric Synthesis of Topographically Constrained Amino Acids: Synthesis of the Optically Pure Isomers of a,B-Dimethyl-Phenylalanine and a,B-Dimethyl-1,2,3,4-Tetrahydroisoquinoline-3-Carboxylic Acid", Tetrahedron Lett., 1991, 32(41):5769-5772.
Kazmierski et al., "Topographic Design of Peptide Neurotransmitters and Hormones on Stable Backbone Templates: Relation of Confirmation and Dynamics to Bioactivity", J. Am. Chem. Soc., 1991, 113:2275-2283.
Kemp et al., "A Convenient Preparation of Derivatives of 3(S)-amino-10(R)-Carboxy-1,6-Diaza-Cyclodeca-2,7-Dione The Dilactam of L-a,y-Diaminobutyric Acid and D-Glutamic Acid A B-Turn Template", Tetrahedron Lett., 1988, 29(40):5057-5060.
Kemp et al., "Amino acid derivatives that stabilize secondary structures of polypeptides. 4. Practical synthesis of 4-(alkylamino)-3-cyano-6-azabicyclo[3.2.1]oct-3-enes (ben derivatives) as .gamma.-turn templates", J. Org. Chem., 1989, 54(1):109-115.
Kemp et al., "Conformational Analysis of Peptide-Functionalized Diacylaminoepindolidiones 1H NMR Evidence for B-Sheet Formation", Tetrahedron Lett., 1988, 29:5081-5082.
Kemp et al., "Conformationally Restricted Cyclic Nonapeptides Derived from L-Cysteine and LL-3-Aminio-2-piperiodone-6-carboxyclic Acid (LL-Acp), a Potent B-Turn-Inducing Dipeptide Analogue", J. Org. Chem., 1985, 50:5834-5838.
Kenny et al., "Production of Monoclonal Antibodies Using a Secretion Capture Report Web", Bio. Technol., 1995, 13:787-790.
Lebkowski et al., "Adeno-Associated Virus: a Vector System for Efficient Introduction and Integration of DNA into a Variety of Mammalian Cell Types", Mol. Cell. Biol., 1988, 8(10):3988-3996.
Liu et al., "Activity of HIV entry and fusion inhibitors expressed by the human vaginal colonizing probiotic Lactobacillus reuteri RC-14", Cellular\Microbiology, 2007, 9(1):120-130.
Liu et al., "Engineered Vaginal Lactobacillus Strain for Mucosal Delivery of the Human Immunodeficiency Virus Inhibitor Cyanovirin-N", Antimicrob. Agents & Chemotherapy, 2006, 50(10):3250-3259.
Mendez et al., "Analysis of the Structural Integrity of YACs Comprising Human Immunoglobulin Genes in Yeast and in Embryonic Stem Cells", Genomics, 1995, 26:294-307.

(56) References Cited

OTHER PUBLICATIONS

Mendez et al., "Functional transplant of megabase human immunoglobulin loci recapitulates human antibody response in mice", Nature Genetics, 1997, 15:146-156.
Miyake et al., "1,2,3,4-Tetrahyudroisoquinoline-3-carboxylic Acid Angiotensin", J. Takeda Res. Labs., 1989, 43:53-76.
Mori et al., "Isolation and Characterization of Griffithsin, a Novel HIV-inactivating Protein, from the Red Alga *Griffithsia* sp.", J. Biol. Chem., 2005, 280(10):9345-9353.
Muller et al., "Estimating Amino Acid Substitution Models: A Comparison of Dayhoff's Estimator, the Resolvent Approach and a Maximum Likelihood Method", Mol. Biol. Evol., 2002, 19:8-13.
Nagai & Sato, "Synthesis of a bicyclic dipeptide with the shape of B-turn central part", Tetrahedron Lett., 1985, 26:647-650.
Nguyen et al., "Production of Human Monoclonal Antibodies in SCID Mouse", Microbiol. Immunol., 1997, 41(12):901-907.
O'Keefe et al., "Scaleable manufacture of HIV-1 entry inhibitor griffithsin and validation of its safety and efficacy as a topical microbicide component", Proc. Nat. Acad. Sci. USA, 2009, 106(15):6099-6104.
Olson et al., "Design and Synthesis of a Protein B-Turn Mimetic", J. Am. Chem. Sci., 1990, 112:323-333.
Padlan et al., "A Possible Procedure for Reducing the Immunogenicity of Antibody Variable Domains While Preserving Their Ligand-Binding Properties", Mol. Immunol., 1991, 28(4/5):489-498.
Papahadjopoulos, D., "Liposomes and Their Use in Biology and Medicine", New York Academy Sciences Meeting, Dec. 1977. (1 page).
PCT International Preliminary Report on Patentability (Chapter 1) for PCT/US2016/041399 dated Jan. 25, 2018. (5 pages).
PCT International Search Report and Written Opinion for PCT/US2016/041399 dated Oct. 6, 2016. (10 pages).
Powell et al., "Gel Microdroplets and Flow Cytometry: Rapid Determination of Antibody Secretion by Individual Cells Within a Cell Population", Biotechnol., 1990, 8:333-337.
Rao et al., "Toward a live microbial microbicide for HIV: Commensal bacteria secreting an HIV fusion inhibitor peptide", PNAS, 2005, 102(34):11993-11998.
Russel et al., "Production of Protective Human Antipneumococcal Antibodies by Transgenic Mice with Human Immunoglobulin Loci", Infection and Immunity, 2000, 68(4):1820-1826.
Samanen et al., "5,5-dimethylthiazolidine-4-carboxylic acid (DTC) as a proline analog with restricted conformation", Int. J. Protein Pep. Res., 1990, 35:501:509.
Sandhu et al., "The Use of SCID Mice in Biotechnology and as a Model for Human Disease", Crit. Rev. Biotechnol., 1996, 16(1):95-118.
Schlesinger & Dubensky, "Alphavirus vectors for gene expression and vaccines", Curr. Opin. Biotechnol., 1999, 5:434-439.
Spira et al., "The Identification of Monoclonal Class Switch Variants by Sib Selection and an ELISA Assay", J. Immunol. Methods, 1984, 74:307-315.
Steenbakkers et al., "Efficient generation of monoclonal antibodies from preselected antigen-specific B cells. Efficient immortalization of preselected B cells", Molec. Biol. Reports, 1994, 19:125-134.
Steplewski et al., "Isolation and characterization of anti-monosialoganglioside monoclonal antibody 19-9 class-switch variants", Proc. Natl. Acad. Sci. USA, 1985, 82:8653-8657.
Tsuda et al., "Inactivation of the mouse HPRT locus by a 203-bp retroposon insertion and a 55-kb gene-targeted deletion: Establishment of a new HPRT-deficient mouse embryonic stem cell lines", Genomics, 1997, 42:413-421.
Wen et al., "Limiting dilution assay for human B cells based on their activation by mutant EL4 thymoma cells: total and antimalarial responder B cell frequencies", J. Immunol., 1987, 17:887-892.
Wickham et al., "Integrins avr33 and av135 promote adenovirus internalization but not virus attachment", Cell, 1993, 73(2):309-319.
Wickman & Nemerow, "Optimization of Growth Methods and Recombinant Protein Production in BTI Tn-5BI-4 Insect Cells using the Baculovirus Expression", Vector. Biotechnol. Prog., 1993, 9(1)25-30.
Wilchek & Bayer, "The avidin-biotin complex in Bioanalytical applications", Anal. Biochem., 1988, 171:1-32.
Yang et al., "Eradication of established tumors by a fully human monoclonal antibody to the epidermal growth factor receptor without concomitant chemotherapy", Cancer Research, 1999, 59(6):1236-1243.
Yang et al., "Fully human anti-interleukin-8 monoclonal antibodies: potential therapeutics for the treatment of inflammatory disease states", J. of Leukocyte Biology, 1999, 66:401-410.
Ying et al., "Cancer therapy using a self-replicating RNA vaccine", Nat. Med., 1999, 5(7):823-827.
Zabrocki et al., "Conformational Mimicry. 1. 1,5-Disubstituted Tetrazole Ring as a Surrogate for the Cis Amide Bond", J. Am. Chem. Soc., 1988, 110:5875-5880.
Zapata et al., "Engineering linear F(ab')2 fragments for efficient production in *Escherichia coli* and enhanced antiproliferative activity", Protein Eng., 1995, 8(10):1057-1062.
Zechel et al., "Synthetic glucagon antagonists and partial agonistst", Int. J. Pep. Protein Res., 1991, 38(2):131-138.

FACTOR VIII PROTEIN COMPOSITIONS AND METHODS OF TREATING OF HEMOPHILIA A

FIELD OF THE INVENTION

The present invention relates generally to recombinant Factor VIII polypeptide compositions and methods for restoring coagulation of blood and for treating hemophilia A.

BACKGROUND

Hemophilia A is a devastating X-linked recessive bleeding disorder occurring in the general population at frequency of 1-2 in 10,000 male births. The disease is caused by genetic changes encoding the blood clotting Factor VIII protein (FVIII). FVIII serves as necessary co-factor for the Factor IXa proteolytic activation of Factor X. Factor X activates thrombin which cleaves fibrinogen into fibrin in order to polymerize and form a blood clot. Genetic changes lead to a deficiency or complete absence of the FVIII activity in plasma. The disease is manifested by soft tissue hematomas and hemarthroses causing life-long permanent disability, shortened life-span, and in some instances, death. Severely affected patients may experience spontaneous internal hemorrhages even without cause of any trauma.

FVIII peptide is significant because of its biochemical properties and pathway. Nearly all plasma FVIII circulates as a complex with von Willebrand factor which is believed to stabilize, protect, and escort the protein to the blood vessel injury site. It has been shown that the delivery of FVIII to the site of injury increases the generation of thrombin and strengthens the plug formed by platelets. FVIII is also relatively large in size and the activation of its precursor involves a tantalizing sequence of post-translational modifications. The processing of FVIII involves proteolytic cleavages at numerous sites as well as other covalent modifications, such as N- and O-linked glycosylation, disulfide bridge formation, tyrosine sulfation, and metal cation insertion. These modifications eventuate in active, but labile protein possessing a plasma half-life of only 8 to 10 hours. An increase of FVIII serum level alleviates the symptoms of severe hemophilia A, leading to less frequent bleeding.

Gene therapy, using viral or plasmid vectors, is a possible avenue for treating hemophilia A. Studies toward this end in animal models are ongoing. Replacement therapy was introduced in the late 1970s and remains the only therapy currently available for Hemophilia A. It requires catheter or intravenous infusion of FVIII protein to compensate for its endogenous deficiency. Alternatively, mild cases of hemophilia A can sometimes be managed by taking desmopressin, which releases stored factor VIII from blood vessel walls. Thus, there remains need for an effective, safe treatment for hemophilia A.

SUMMARY

Factor VIII protein used for replacement therapy is commonly produced in the form of a concentrate that is cryo-precipitated from the plasma of healthy individuals (usually, ~1000-4000 L of human plasma pooled from >100,000 donations, is required for industrial scale production. Alternatively, FVIII is prepared as a recombinant protein expressed and purified from mammalian cells. Infusion treatments usually maintain FVIII levels above 2 ng/ml, sufficient to reduce hemorrhages. Unfortunately, because of the short half-life of FVIII, two to three intravenous administrations of FVIII protein per week are often required. A significant drawback to current therapy is the fact that nearly one out of four patients develop inhibitory alloantibodies against FVIII. Anti-FVIII antibodies often reach extremely high titers and the application of immune-tolerance therapy requiring more than a year-long administration of larger amounts of FVIII does not often surpass the inhibition. The average cost of the current monthly treatment is about $11,000 per patient. For those who develop inhibitory antibodies, the cost can increase to an astonishing $50,000 per month. Obviously, this is beyond the means of most families, as well as many insurers, especially those from undeveloped and developing countries. Another obstacle is the chronic shortage of FVIII supply, despite decades of efforts by pharmaceutical giants like Baxter, Bayer, and Pfizer. Presently, these companies continue attempts to meet the growing demands for recombinant FVIII. Thus, access to hemophilia A treatment possesses a dramatic socioeconomic component as well.

Provided herein are the recombinant synthesis, Factor X activation, Factor IXa activation, thrombin activation, and coagulative properties of a recombinant Factor VIII protein (rFVIII) and its therapeutic compositions. Herein, site-directed mutagenesis provides recombinant Factor VIII protein modified at the interface of the A1-A3 domain. This variant possesses an improved pharmacokinetic profile, i.e. a longer plasma resident half-life and will allow for less frequent injections during treatment, thereby improving the quality of life to patients suffering from hemophelia A.

In one aspect, provided herein is a recombinant Factor VIII protein modified at the A1-A3 domain interface by substitution of one or more residues selected from the group consisting of Val120, Leu178, Ser1978, Glu2018, and Leu2020 with at least one copper or zinc ion chelating amino acid. Further, said recombinant FVIII protein may be optionally modified to exclude and/or alter the sequence of the B domain of the peptide. The entire wild-type FVIII protein sequence is known and its replication has been reported in numerous patents and specifically by PCT/US2013/026521, the contents of which are herein incorporated by reference. The skilled artisan is able to use these or other methods known in the art to reproduce this peptide sequence with modifications to the afore amino acid residues in order to incorporate chelating amino acids at those positions.

In another aspect, provided herein is a method for activating Factor X (FX) which, in turn, promotes the coagulation cascade via activation of thrombin. Activated Thrombin cleaves fibrinogen into fibrin. Fibrin uses factor XIII to crosslink and form into a blood clot. An essential step in is the interaction of FVIII with Factor IXa in order to accelerate the sequence. The method herein provides for a recombinant variant FVIII with improved stability and capability to interact as a cofactor of Factor IXa and efficiently activate FX. The method comprises, or alternatively consists essentially of, or yet further consists of, infusing a subject's circulatory system with a composition, or a pharmaceutical composition, including an isolated or recombinant FVIII polypeptide comprising amino acid residues capable of chelating at least one copper or zinc ion, or at least two copper or zinc ions, or at three copper or zinc ions, or a biological equivalent thereof. In one aspect, the isolated or recombinant polypeptide is not simply the wild-type Factor VIII peptide. The polypeptide can be substituted at one or more or all amino acid residues selected from the group consisting Val120, Leu178, Ser1978, Glu2018, and Leu2020 with a copper or zinc ion chelating amino acid by natural or chemical methods, e.g., by a commercially available method. In another aspect, the isolated or recombinant polypeptide further comprises, or alternatively consists essentially of, or yet further consists of, recombinant FVIII peptide capable of chelating at least one copper or zinc ion, or at least two or more copper or zinc cations. A non-limiting example of such is a recombinant polypeptide comprising, or alternatively consisting essentially of, or yet further consisting of a FVIII protein substituted at each of the Val120, Leu178, Ser1978, Glu2018, and Leu2020 residues with a histidine residue, or a biological equivalent thereof.

In a further aspect, the methods further comprises, or alternatively consists essentially of, or yet further consists of, contacting a patient's circulatory system with an agent that inhibits the proteolytic degradation, or any other kind of degradation, of FVIII by protease activated protein C (APC) or other such enzymes or proteins. In one aspect, the isolated or recombinant polypeptide is not simply the wild-type FVIII peptide. The method comprises, or alternatively consists essentially of, or yet further consists of, infusing a subject's circulatory system with a composition, or a pharmaceutical composition, including an isolated or recombinant polypeptide FVIII, or a biological equivalent thereof.

In another embodiment, provided is a method of treating a condition mediated or caused by the proteolytic degradation of FVIII, comprising, alternatively consisting essentially of, or yet further consisting of, administering to the subject an effective amount of with a composition, or a pharmaceutical composition, including an isolated or recombinant polypeptide FVIII, or a biological equivalent thereof. In one aspect, the isolated or recombinant polypeptide is not simply the wild-type FVIII peptide. In another aspect the recombinant FVIII polypeptide is substituted by substitution of one or more residues selected from the group consisting of Val120, Leu178, Ser1978, Glu2018, and Leu2020 with a copper or zinc ion chelating amino acid. Further, said recombinant FVIII protein may be optionally modified to exclude and/or alter the sequence of the B domain of the peptide. The polypeptide can be substituted at one or more domains by natural or chemical methods, e.g., by a commercially available method.

In each of the above embodiments, the recombinant variant FVIII protein can also be delivered by gene therapy methods which comprise, or alternatively consist essentially of, or yet further consist of, administering or contacting a subject's circulatory system with an isolated or recombinant polynucleotide encoding the isolated recombinant FVIII protein.

Compositions, or a pharmaceutical compositions, for use in the methods are further provided herein. For example, an isolated or recombinant polypeptide comprising, or alternatively consisting essentially of, or yet further consisting of, recombinant Factor VIII protein modified at the A1-A3 domain interface by substitution of one or more residues selected from the group consisting of Val120, Leu178, Ser1978, Glu2018, and Leu2020 with one or more copper or zinc ion chelating amino acids. Further, said recombinant FVIII protein may be optionally modified to exclude and/or alter the sequence of the B domain of the peptide, or a biological equivalent thereof is provided. Optionally, a pharmaceutically acceptable carrier may be included in such a composition. In one aspect the polypeptide is capable of chelating at least one copper or zinc ion, or at least two copper or zinc ions, or three copper or zinc ions, or a biological equivalent thereof. The recombinant polypeptide can be substituted at one or more amino acid residues by natural or chemical methods, e.g., by a commercially available method.

The polypeptides or polynucleotides encoding the recombinant FVIII are provided for herein and can further comprise a detectable label.

Compositions comprising a carrier and one or more of the polypeptides, polynucleotides and expression or delivery vectors are further provided herein. The carrier can be a solid support or a liquid carrier such as a pharmaceutically acceptable carrier.

Antibodies that recognize and bind an isolated or recombinant polypeptide and/or an isolated or recombinant polynucleotide are further provided. The antibodies can be used to isolate polynucleotides or polypeptides. The antibody is any of a polyclonal antibody, a monoclonal antibody, an antibody fragment such as a CDR, a chimeric antibody, an antibody derivative, a recombinant humanized antibody, recombinant antibody, a human antibody, a veneered antibody or a humanized antibody. Polynucleotides encoding the antibody and host cells containing the isolated recombinant polynucleotides are further provided by this invention. The host cells can be used to recombinantly produce the antibody polypeptides by growing the host cell containing an isolated or recombinant polynucleotide under conditions that favor the expression of the antibody expressing polynucleotide. In one aspect, the polypeptide is isolated from the host cell. Yet further provided is an antibody complex comprising the antibody of this invention and a polypeptide or polynucleotide specifically bound to the antibody. A hybridoma cell line that produces the monoclonal antibody is also provided.

Compositions comprising a carrier and one or more of the antibody or polynucleotide encoding the antibody are further provided herein. The carrier can be a solid support or a liquid carrier such as a pharmaceutically acceptable carrier.

The antibodies, fragments, and isolated polynucleotides encoding the recombinant FVIII are provided for herein and can further comprise a detectable label.

Further provided by this invention is a kit comprising one or more of an isolated or recombinant polypeptide of this invention, an isolated or recombinant polynucleotide of this invention, or an isolated antibody or fragment thereof, of any of this invention and instructions for use. The instructions can be for use of the compositions of this invention for therapeutic, diagnostic or to screen for new therapeutic agents.

Screens to identify new therapeutic agents are also provided. The method comprises screening for an agent that inhibits or interferes with the activation of FX, thrombin, and/FIXa, by contacting a eukaryotic cell expressing FVIII with the agent and assaying for FX, thrombin, and/or FIXa function. In one aspect, the eukaryotic cell is a blood cell. The screen can further comprise, or alternatively consist essentially of, or yet further consist of comparing FX, thrombin, and/or FIXa function of the eukaryotic cell with the ability of an isolated or recombinant polypeptide or the isolated or recombinant polynucleotide of this invention to induce wound healing.

DETAILED DESCRIPTION

The concentration of FVIII in a normal healthy individual's plasma is about 0.2 µm/ml and only 1% of which (2 ng/ml) is already sufficient to achieve a moderate phenotype. An increase of FVIII level to or slightly above the 1% usually ameliorates the symptoms of severe form of hemophilia A leading to less frequent bleeding.

FVIII, however, is resistant toward an efficient expression in heterologous systems, which hinders the production of FVIII in quantities sufficient to lower the cost of treatment. Several factors causing low levels of FVIII expression have been identified and include: (i) instability of the mRNA, (ii) misfolding and intracellular degradation of the protein in the lumen of ER, and (iii) lability of the secreted protein leading to its rapid proteolytic degradation. Indeed, FVIII is several orders of magnitude lower in concentration than plasma proteins of comparable size, including ceruloplasmin. The roadmap for expression of this disorder resides in the genetic transcription of FVIII; and therein lies a story of evolutionary divergence possessing an interesting opportunity.

The gene for FVIII, at 192 kb, is one of the largest on the X-chromosome. It transcribes the 9 kb mRNA, which displays suboptimal stability. The FVIII precursor protein is composed of 2,351 amino acids organized by: a 19 amino acids signal peptide (SP), triplicated A-domains which are about 330 amino acids in length, a single, roughly 900 amino acid B-domain located between the A2 and A3 domains, and duplicated C-domains about 150 amino acids in length. Additionally, the A and B domains are spaced from each other by a 40 amino acid long, negatively charged segment often labeled as a1, a2, and a3. Thus, the full-length precursor is made in the following order of domain organization: SP-A1-a1-A2-a2-B-a3-A3-C1-C2. The A-domains possess duplicated cupredoxin folds with the analogous domains of cupredoxin, the B-domain displays no sequence conservation with FVIII proteins from other species, and the C-domains belong to discoidin fold superfamily, which are known to bind acidic phospholipids.

Ceroplasmin can be considered an ancestral analog to FVIII protein. Ceruloplasmin (CP) is a stable metalloprotein, the concentration of which in plasma increases in response to inflammation. It belongs to a diverse family of ubiquitous enzymes known as multi-copper or zinc oxidases (MCOs). Cupredoxin folds, crucial to Ceruplasmin stability, are generally anywhere from 100-200 amino acids in length and are characterized by their high structural stability, especially in their holo-, metal bound form. This thermodynamically stable structure usually houses the mononuclear copper binding site in the so-called "blue" configuration. Ceruloplasmin possesses three such copper binding sites, located in cupredoxin domains 2, 4, and 6. Factor VIII maintains only two, residing in cupredoxin folds 2 and 6.

Eight Histidine residues serve as ligands for trinuclear copper or cluster of CP. All eight Histidine ligands are provided by A1 (cupredoxin domain 1) and A3 (cupredoxin domain 6) sequence domains, and thus providing additional structural stability at domain-domain interface. These non-covalent interactions at the domain interface play crucial role in the stability of CP and other members of MCO family, however they are absent in FVIII protein. Herein it is recognized that the loss of thermodynamic stabilization, provided by these copper or zinc binding sites, that is the main cause behind FVIII protein's short half-life in blood stream. A similar situation manifests in individuals suffering with Wilson's disease, which is characterized by loss of CP activity caused by impaired metallation and consequently leading to rapid proteolytic degradation of its apo-form, decreasing its half-life nearly 26 fold.

In-vivo, Factor VIII is generally cleared from circulation by various proteases. FVIII exists, much of the time, in the form of a heterodimer, consisting of both heavy and light chains. FVIII is usually observed bound to von Willebrand factor (vWF). VWF bindes to FVIII residues 1649-1689 and the C2 domain. Activation from thrombin includes the cleavage of the 1689 peptide bond and signals dissociation of FVIII from vWF. This event accelerates the cascade that will eventually lead to coagulation. Among the residues that FVIII binds to, and therefore enhances FIXa activity and subsequently the activation of FX are residues 558-565 and 349-372, respectively. The protease activated protein C (APC) proteolytically degrades FVIII thru residues 336 and 562. Specifically, the mechanism of this degradation excises the A2 domain from A1 and A3-C1-C2 domain interface. Thus, the present invention provides, by thermodynamically stabilizing FVIII, a decrease in proteolytic degradation of FVIII. In turn, an increase in FVIII half-life is observed which promotes blood coagulation via stimulating FIXa activity, which further leads to FX and thrombin activation.

Herein the invention demonstrates that the recombinant FVIII, modified by point mutation, stimulates FX and FIXa activation. In turn, this activation leads to increases of thrombin and blood coagulation. Thus, the recombinant Factor VIII substantially decreases the frequency and cost of replacement therapy for patients suffering with hemophilia A.

The amino acid sequence of wild-type FVIII protein is very well known in the art and has been described in for example US 20130085110 A1, which is herein incorporated by reference. In lieu of listing the entire sequence for the wild-type and recombinant FVIII peptides, reference is made to the afore mentioned example. The FVIII sequence is also available electronically via the Haemophilia A Mutation, Structure, Test and Resource Site (or HAMSTeRS), which further provides an alignment of human, porcine, murine, and canine Factor VIII proteins. Thus, the conservation and homology among mammalian Factor VIII proteins is well known.

In one embodiment, the invention is recombinant FVIII protein reconstituted with the ancestral trinuclear copper or zinc binding site located at the interface of A1 and A3 sequence domains, based on analogy with paralog CP. In another embodiment, factor X and/or blood coagulation is restored thru reconstituting copper or zinc binding in the recombinant FVIII protein.

Relatively recent scientific literature has described methods to increase FVIII expression efficiency by truncating or deleting the B-domain. Such procedures have indeed demonstrated that the B domain is dispensible and readily altered without affecting the natural activity of FVIII. Thus, in another embodiment, it is contemplated that the present invention is fully capable of comprising a shortened, altered, point mutated, and linker conjugated B-domain. An example of, but certainly not limited to, such a modification is recombinant FVIII comprising an attachment of polyethylene glycol polymeric chains to the B-domain.

In yet another embodiment, it is contemplated that the present invention may be formulated and thereby stabilized with, but not limited to, additives comprising albumin, sucrose, or other non-human derived components.

In yet another embodiment, a biologically active, recombinant factor VIII (FVIII) polypeptide comprising the amino acid sequence of wild-type human FVIII protein wherein said sequence has been modified at one or more residues selected from the group consisting of Val120, Leu178, Ser1978, Glu2018, and Leu2020 with a copper or zinc ion chelating amino acid such that the biologically active recombinant factor VIII polypeptide chelates at least two copper or zinc ions.

In yet another embodiment, the recombinant FVIII polypeptide is capable to chelate at least three copper or zinc cations.

In yet another embodiment, the recombinant FVIII polypeptide comprising amino acid substitution at two or more residues selected from the group consisting of Val120, Leu178, Ser1978, Glu2018, and Leu2020.

In yet another embodiment, the recombinant FVIII polypeptide comprising amino acid substitution for all residues of Val120, Leu178, Ser1978, Glu2018, and Leu2020.

In yet another embodiment, the recombinant FVIII polypeptide wherein the amino acid substitution is substitution with an amino acid selected from the group consisting of histidine, lysine, cysteine, methionine, proline, tryptophan, tyrosine, arginine, asparginine, glutamine, aspartic acid, and glutamic acid.

In yet another embodiment, the recombinant FVIII polypeptide wherein the amino acid substitution is substitution with histidine.

In yet another embodiment, the recombinant FVIII polypeptide wherein the polypetide is post-translationally modified with an organic functional group that chelates at least one copper or zinc ion.

In yet another embodiment, the recombinant FVIII polypeptide wherein the substitution is with any amino acid derivative that is functionalized with a nucleobase or an organic functional group selected from the group consisting of carboxylic acid, amine, amide, imine, guanidine, carbamate, porphyrin, chlorin, corrin, crown ether, cryptand, imidazole, pyrrole, piperidine, pyrrroldine, pyridine, thiol, sulfonic acid, sulfonate, and sulfamide or any such functional group that might react under physiological conditions in order to form said organic functional groups.

In yet another embodiment, the recombinant FVIII polypeptide wherein the homology has at least 95% sequence identity to that of the wild-type FVIII protein, respectively.

In yet another embodiment, the recombinant polypeptide which includes a B domain that is modified from the B domain of the wild type FVIII polypeptide.

In yet another embodiment, a recombinant polypeptide that is modified from the B domain and possesses an amino acid sequence having at least 90% sequence identity.

In yet another embodiment, the recombinant polypeptide which does not include a B domain.

In yet another embodiment, the peptide resulting from degradation of the recombinant FVIII polypeptide.

In yet another embodiment, a recombinant polynucleotide comprising a nuclei acid sequence encoding the recombinant FVIII polypeptide.

In yet another embodiment, a host cell comprising the recombinant polynucleotide comprising a nuclei acid sequence encoding the recombinant FVIII polypeptide.

In yet another embodiment, synthetic blood comprising the recombinant FVIII polypeptide or synthetic blood comprising the degredation product product of FVIII.

In yet another embodiment, a method for enhancing or restoring blood coagulation in a patient in need therefore, comprising administering to the patient an effective amount of the recombinant FVIII polypeptide, or administering the degradation product product of FVIII or the synthetic blood comprising the recombinant FVIII polypeptide or comprising the degredation product product of FVIII.

In yet another embodiment, the method a method for enhancing or restoring blood coagulation in a patient in need therefore, comprising administering to the patient an effective amount of the recombinant FVIII polypeptide, or administering the degredation product product of FVIII or the synthetic blood comprising the recombinant FVIII polypeptide or comprising the degradation product product of FVIII, wherein the patient suffers from mild or severe, internal or external, bleeding.

In yet another embodiment, a method for treating hemophilia A, comprising administering to a patient an effective amount of the recombinant FVIII polypeptide, the degradation product of the recombinant FVIII polypeptide, or the synthetic blood comprising the recombinant FVIII polypeptide or comprising the degredation product product of FVIII.

In yet another embodiment, an antibody that specifically recognizes the recombinant FVIII polypeptide, but does not recognize wild-type FVIII protein.

In yet another embodiment, an isolated or recombinant polynucleotide encoding the antibody that specifically recognizes the recombinant FVIII polypeptide.

Definitions

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

All numerical designations, e.g., pH, temperature, time, concentration, and molecular weight, including ranges, are approximations which are varied (+) or (−) by increments of 1.0 or 0.1, as appropriate. It is to be understood, although not always explicitly stated, that all numerical designations are preceded by the term "about". It also is to be understood, although not always explicitly stated, that the reagents described herein are merely exemplary and that equivalents of such are known in the art.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above.

As used in the specification and claims, the singular form "a", "an" and "the" include plural references unless the context clearly dictates otherwise. For example, the term "a pharmaceutically acceptable carrier" includes a plurality of pharmaceutically acceptable carriers, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "subject" of diagnosis or treatment is a cell or an animal such as a mammal, or a human. Non-human animals subject to diagnosis or treatment are, for example, simians, murine, such as, rats, mice, canine, such as dogs, leporids, such as rabbits, livestock, such as bovine or ovine, sport animals, such as equine, and pets, such as canine and feline.

A "chimeric polypeptide", "chimeric protein" or "fusion protein" refers to a protein, peptide or polypeptide created through the joining of two or more amino acid sequences or alternatively created by expression of a joint nucleotide sequence comprising two or more nucleotide sequences which originally code for separate proteins, peptides, polypeptides. Translation of joined nucleotide sequence, also known as a fusion gene, results in a single polypeptide, the "chimeric polypeptide", with functional properties derived from each of the original proteins.

The terms "protein", "peptide", and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, interfering RNA (RNAi), messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

"Double stranded RNA" (dsRNA) refer to double stranded RNA molecules that may be of any length and may be cleaved intracellularly into smaller RNA molecules, such as siRNA. In cells that have a competent interferon response, longer dsRNA, such as those longer than about 30 base pair in length, may trigger the interferon response. In other cells that do not have a competent interferon response, dsRNA may be used to trigger specific RNAi.

"shRNA" is short hairpin RNA.

microRNA or miRNA are single-stranded RNA molecules of 21-23 nucleotides in length, which regulate gene expression. miRNAs are encoded by genes from whose DNA they are transcribed but miRNAs are not translated into protein (non-coding RNA); instead each primary transcript (a pri-miRNA) is processed into a short stem-loop structure called a pre-miRNA and finally into a functional miRNA. Mature miRNA molecules are partially complementary to one or more messenger RNA (mRNA) molecules, and their main function is to down-regulate gene expression.

The term "isolated" as used herein with respect to nucleic acids, such as DNA or RNA, refers to molecules separated from other DNAs or RNAs, respectively that are present in the natural source of the macromolecule. The term "isolated nucleic acid" is meant to include recombinant polynucleotides and nucleic acid fragments which are not naturally occurring as fragments and would not be found in the natural state. The term "isolated" is also used herein to refer to polypeptides and proteins that are isolated from other cellular proteins and is meant to encompass both purified and recombinant polypeptides. In other embodiments, the term "isolated" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. As is apparent to those of skill in the art, a non-naturally occurring polynucleotide, peptide, polypeptide, protein, antibody or fragment(s) thereof, does not require "isolation" to distinguish it from its naturally occurring counterpart.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together. A non-limiting example of such is the recombinant factor VIII (FVIII) polypeptide comprising the amino acid sequence of wild-type human FVIII protein wherein said sequence has been substituted at the Val120, Leu178, Ser1978, Glu2018, and Leu2020 residues with a hisitidine residues, and further the polynucleotide that encodes it.

As used herein, the term "biological equivalent thereof" is used synonymously with "equivalent" unless otherwise specifically intended. When referring to a reference protein, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 60%, or 65%, or 70%, or 75%, or 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid. Alternatively, a biological equivalent is a peptide encoded by a nucleic acid that hybridizes under stringent conditions to a nucleic acid or complement that encodes the peptide. Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

A polynucleotide or polynucleotide region (or a polypeptide or polypeptide region) having a certain percentage (for example, about 60%, 65%, 70%, 75%, 80%, 85%, 90%, 95% or 97%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is CLUSTAL or BLAST, using default parameters. In particular, preferred programs are CLUSTAL, BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

An "equivalent" of a polynucleotide or polypeptide refers to a polynucleotide or a polypeptide having a substantial homology or identity to the reference polynucleotide or polypeptide. In one aspect, a "substantial homology" is greater than about 60%, 65%, 70%, 75%, 80%, 85%, 90%, 95% or 98% homology.

As used herein, "expression" refers to the process by which polynucleotides are transcribed into precursor RNA and/or the process by which it is transcribed mRNA is subsequently being translated into peptides, polypeptides, or proteins. If the polynucleotide is derived from nuclear DNA, expression includes splicing of the precursor RNA into mRNA in the nucleus of an eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

"Regulatory polynucleotide sequences" intends any one or more of promoters, operons, enhancers, as know to those skilled in the art to facilitate and enhance expression of polynucleotides.

An "expression vehicle" is a vehicle or a vector, non-limiting examples of which include viral vectors or plasmids, that assist with or facilitate expression of a gene or polynucleotide that has been inserted into the vehicle or vector.

A "delivery vehicle" is a vehicle or a vector that assists with the delivery of an exogenous polynucleotide into a target cell. The delivery vehicle may assist with expression or it may not, such as traditional calcium phosphate transfection compositions.

A "composition" is intended to mean a combination of active agent and another compound or composition, inert (for example, a solids support or pharmaceutically acceptable carrier) or active, such as an adjuvant.

A "pharmaceutical composition" is intended to include the combination of an active agent with a carrier, inert or active, making the composition suitable for diagnostic or therapeutic use in vitro, in vivo or ex vivo.

"An effective amount" refers to the amount of an active agent or a pharmaceutical composition sufficient to induce a desired biological and/or therapeutic result. That result can be alleviation of the signs, symptoms, or causes of a disease, or any other desired alteration of a biological system. The effective amount will vary depending upon the health condition or disease stage of the subject being treated, timing of administration, the manner of administration and the like, all of which can be determined readily by one of ordinary skill in the art.

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder.

As used herein, to "treat" further includes systemic amelioration of the symptoms associated with the pathology and/or a delay in onset of symptoms. Clinical and subclinical evidence of "treatment" will vary with the pathology, the subject and the treatment.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, injection, topical application, intrapentoneal, intravenous and by inhalation. An agent of the present invention can be administered for therapy by any suitable route of administration. It will also be appreciated that the preferred route will vary with the condition and age of the recipient, and the disease being treated.

The agents and compositions of the present invention can be used in the manufacture of medicaments and for the treatment of humans and other animals by administration in accordance with conventional procedures, such as an active ingredient in pharmaceutical compositions.

The term "conjugated moiety" refers to a moiety that can be added to an isolated polypeptide by forming a covalent bond with a residue of polypeptide. The moiety may bond directly to a residue of the polypeptide or may form a covalent bond with a linker which in turn forms a covalent bond with a residue of the polypeptide.

A "peptide conjugate" refers to the association by covalent or non-covalent bonding of one or more polypeptides and another chemical or biological compound. In a non-limiting example, the "conjugation" of a polypeptide with a chemical compound results in improved stability or efficacy of the polypeptide for its intended purpose. In one embodiment, a peptide is conjugated to a carrier, wherein the carrier is a liposome, a micelle, or a pharmaceutically acceptable polymer.

As used herein, the term "detectable label" intends a directly or indirectly detectable compound or composition that is conjugated directly or indirectly to the composition to be detected, e.g., N-terminal histadine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, luminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals ($6^{th}$ ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals ($6^{th}$ ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

"Liposomes" are microscopic vesicles consisting of concentric lipid bilayers that are suitable expression or delivery vehicles. Structurally, liposomes range in size and shape from long tubes to spheres, with dimensions from a few hundred Angstroms to fractions of a millimeter. Vesicle-forming lipids are selected to achieve a specified degree of fluidity or rigidity of the final complex providing the lipid composition of the outer layer. These are neutral (cholesterol) or bipolar and include phospholipids, such as phosphatidylcholine (PC), phosphatidylethanolamine (PE), phosphatidylinositol (PI), and sphingomyelin (SM) and other types of bipolar lipids including but not limited to dioleoylphosphatidylethanolamine (DOPE), with a hydrocarbon chain length in the range of 14-22, and saturated or with one or more double C=C bonds. Examples of lipids capable of producing a stable liposome, alone, or in combination with other lipid components are phospholipids, such as hydrogenated soy phosphatidylcholine (HSPC), lecithin, phosphatidylethanolamine, lysolecithin, lysophosphatidylethanol-amine, phosphatidylserine, phosphatidylinositol, sphingomyelin, cephalin, cardiolipin, phosphatidic acid, cerebrosides, distearoylphosphatidylethanolamine (DSPE), dioleoylphosphatidylcholine (DOPC), dipalmitoylphosphatidylcholine (DPPC), palmitoyloleoylphosphatidylcholine (POPC), palmitoyloleoylphosphatidylethanolamine (POPE) and dioleoylphosphatidylethanolamine 4-(N-maleimido-methyl)cyclohexane-1-carboxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, and the cationic lipids mentioned above (DDAB, DODAC, DMRIE, DMTAP, DOGS, DOTAP (DOTMA), DOSPA, DPTAP, DSTAP, DC-Chol). Negatively charged lipids include phosphatidic acid (PA), dipalmitoylphosphatidylglycerol (DPPG), dioleoylphosphatidylglycerol and (DOPG), dicetylphosphate that are able to form vesicles. Typically, liposomes can be divided into three categories based on their overall size and the nature of the lamellar structure. The three classifications, as developed by the New York Academy Sciences Meeting, "Liposomes and Their Use in Biology and Medicine," December 1977, are multi-lamellar vesicles (MLVs), small uni-lamellar vesicles (SUVs) and large uni-lamellar vesicles (LUVs).

A "micelle" is an aggregate of surfactant molecules dispersed in a liquid colloid. A micelle is an example of a delivery or expression vehicle. A typical micelle in aqueous solution forms an aggregate with the hydrophilic "head" regions in contact with surrounding solvent, sequestering the hydrophobic tail regions in the micelle center. This type of micelle is known as a normal phase micelle (oil-in-water micelle). Inverse micelles have the head groups at the center with the tails extending out (water-in-oil micelle). Micelles can be used to attach a polynucleotide, polypeptide, antibody or composition described herein to facilitate efficient delivery to the target cell or tissue.

The phrase "pharmaceutically acceptable polymer" refers to the group of compounds which can be conjugated to one or more polypeptides described here. It is contemplated that the conjugation of a polymer to the polypeptide is capable of extending the half-life of the polypeptide in vivo and in vitro. Non-limiting examples include polyethylene glycols, polyvinylpyrrolidones, polyvinylalcohols, cellulose derivatives, polyacrylates, polymethacrylates, sugars, polyols and mixtures thereof.

"Pharmaceutically acceptable carriers" refers to any diluents, excipients, or carriers that may be used in the compositions of the invention. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They are preferably selected with respect to the intended form of administration, that is, oral tablets, capsules, elixirs, syrups and the like, and consistent with conventional pharmaceutical practices.

A "gene delivery vehicle" is defined as any molecule that can carry inserted polynucleotides into a host cell. Examples of gene delivery vehicles are liposomes, micelles pharmaceutically acceptable polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide of this invention can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmic vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacteria produces proteins to confer its antibiotic resistance, it can also be induced to produce large amounts of proteins from the inserted gene. This is a cheap and easy way of mass-producing a gene or the protein it then codes for.

A "yeast artificial chromosome" or "YAC" refers to a vector used to clone large DNA fragments (larger than 100 kb and up to 3000 kb). It is an artificially constructed chromosome and contains the telomeric, centromeric, and replication origin sequences needed for replication and preservation in yeast cells. Built using an initial circular plasmid, they are linearised by using restriction enzymes, and then DNA ligase can add a sequence or gene of interest within the linear molecule by the use of cohesive ends. Yeast expression vectors, such as YACs, YIps (yeast integrating plasmid), and YEps (yeast episomal plasmid), are extremely useful as one can get eukaryotic protein products with posttranslational modifications as yeasts are themselves eukaryotic cells, however YACs have been found to be more unstable than BACs, producing chimeric effects.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffithsin in tobacco leaves (O'Keefe et al. (2009) Proc. Nat. Acad. Sci. USA 106(15):6099-6104). Alphavirus vectors, such as Semliki Forest virus-based vectors and Sindbis virus-based vectors, have also been developed for use in gene therapy and immunotherapy. See, Schlesinger & Dubensky (1999) Curr. Opin. Biotechnol. 5:434-439 and Ying et al. (1999) Nat. Med. 5(7):823-827. In aspects where gene transfer is mediated by a retroviral vector, a vector construct refers to the polynucleotide comprising the retroviral genome or part thereof, and a therapeutic gene.

As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., International PCT Application No. WO 95/27071. Ads do not require integration into the host cell genome. Recombinant Ad derived vectors, particularly those that reduce the potential for recombination and generation of wild-type virus, have also been constructed. See, International PCT Application Nos. WO 95/00655 and WO 95/11984. Wild-type AAV has high infectivity and specificity integrating into the host cell's genome. See, Hermonat & Muzyczka (1984) Proc. Natl. Acad. Sci. USA 81:6466-6470 and Lebkowski et al. (1988) Mol. Cell. Biol. 8:3988-3996.

Vectors that contain both a promoter and a cloning site into which a polynucleotide can be operatively linked are known in the art. Such vectors are capable of transcribing RNA in vitro or in vivo, and are commercially available from sources such as Stratagene (La Jolla, Calif.), Novagen/EMDBiosciences, Invitrogen/Life technologies, and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods of this invention. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins of this invention are other non-limiting techniques.

Examples of solid phase supports include glass, polystyrene, polypropylene, polyethylene, dextran, nylon, amylases, natural and modified celluloses, polyacrylamides, gabbros, and magnetite. The nature of the carrier can be either soluble to some extent or insoluble. The support material may have virtually any possible structural configuration so long as the coupled molecule is capable of binding to a polynucleotide, polypeptide or antibody. Thus, the support configuration may be spherical, as in a bead, or cylindrical, as in the inside surface of a test tube, or the external surface of a rod. Alternatively, the surface may be flat such as a sheet, test strip, etc. or alternatively polystyrene beads. Those skilled in the art will know many other suitable carriers for binding antibody or antigen, or will be able to ascertain the same by use of routine experimentation.

"Eukaryotic cells" comprise all of the life kingdoms except monera. They can be easily distinguished through a membrane-bound nucleus and other organelles. Animals, plants, fungi, and protists are eukaryotes or organisms whose cells are organized into complex structures by internal membranes and a cytoskeleton. The most characteristic membrane-bound structure is the nucleus. A eukaryotic host, including, for example, yeast, higher plant, insect and mammalian cells. Non-limiting examples include simian, bovine, ovine, porcine, murine, rats, canine, equine, feline, avian, reptilian and human.

"Prokaryotic cells" that lack a nucleus or any other membrane-bound organelles and are divided into two domains, bacteria and archaea. Instead of having a linear chromosomal DNA, these cells' genetic information is in a circular loop. Additionally, bacteria house extra-chromosomal DNA called a plasmid, which are also circular but very small in size compared to that of chromosomal DNA. These small genetic units are main conduits for transferring DNA material between different types of monera. Bacterial cells are very small, roughly the size of an animal mitochondrion (about 1-2 µm in diameter and 10 µm long). Prokaryotic cells feature three major shapes: rod shaped, spherical, and spiral. Instead of going through elaborate replication processes like eukaryotes, bacterial cells divide by binary fission. Examples include but are not limited to prokaryotic Cyanobacteria, *bacillus* bacteria, *E. coli* bacterium, and *Salmonella* bacterium.

As used herein, an "antibody" includes whole antibodies and any antigen binding fragment or a single chain thereof. Thus the term "antibody" includes any protein or peptide containing molecule that comprises at least a portion of an immunoglobulin molecule, i.e., an antibody fragment. Examples of antibody fragments include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The antibodies can be polyclonal or monoclonal and can be isolated from any suitable biological source, e.g., murine, rat, sheep, rabbit, and canine.

The term "human antibody" as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

A "human monoclonal antibody" refers to antibodies displaying a single binding specificity which have variable and constant regions derived from human germline immunoglobulin sequences. The term also intends recombinant human antibodies. Methods to making these antibodies are described herein.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. Methods to making these antibodies are described herein.

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope.

The terms "monoclonal antibody" or "monoclonal antibody composition" as used herein refer to a preparation of antibody molecules of single molecular composition from a hybridoma. A monoclonal antibody composition displays a single binding specificity and affinity for a particular epitope.

Descriptive Embodiments

Therapeutic Methods

The present invention provides a method for imparing the proteolytic degradation of Factor VIII protein in the circulatory system. In one aspect, the degradation is caused by the action of peptide C on FVIII. The method comprises, or alternatively consists essentially of, or yet further consists of, contacting the cell with an isolated or recombinant Factor VIII, or a biological equivalent thereof. In one aspect, the isolated or recombinant polypeptide is not simply the wild-type FVIII protein in a mammalian cell system. In another aspect, the isolated or recombinant polypeptide further comprises, or alternatively consists essentially of, or yet further consists of, an agent that stabilizes FVIII in the composition. A non-limiting example of such is a polypeptide comprising, or alternatively consisting essentially of, or yet further consisting of, a composition including an isolated or recombinant polypeptide FVIII and albumin, or a biological equivalent thereof. Such agents are known to those of skill in the art, e.g., sucrose.

In another embodiment, this invention provides a method of treating a condition in a subject in need thereof and mediated by FX and FIXa activation, comprising, or alternatively consisting essentially of, or yet further consisting of, administering to the subject an effective amount of an isolated or recombinant polypeptide comprising or alternatively consisting essentially of, or yet further consisting of a composition including an isolated or recombinant polypeptide FVIII, or a biological equivalent thereof. In one aspect, the isolated or recombinant polypeptide is not simply the wild-type FVIII protein. In another aspect, the isolated peptide further comprises, or alternatively consists essentially of, or yet further consists of, an agent that stabilizes FVIII in the composition. A non-limiting example of such is a polypeptide comprising, or alternatively consisting essentially of, or yet further consisting of, a composition including an isolated or recombinant polypeptide FVIII and albumin, or a biological equivalent thereof. Such agents are known to those of skill in the art, e.g., sucrose.

In a yet further embodiment, this invention provides a method of activating thrombin, FX, and/or FIXa in a eukaryotic cell in a subject in need thereof, comprising, or alternatively consisting of, or yet further consisting of, administering to the subject an effective amount of an isolated or recombinant polypeptide comprising or alternatively consisting essentially of, or yet further consisting of, a composition including an isolated or recombinant polypeptide FVIII, or a biological equivalent thereof. In one aspect, the isolated or recombinant polypeptide is not simply the wild-type FVIII in a mammalian cell system. In another aspect, the isolated peptide further comprises, or alternatively consists essentially of, or yet further consists of, an agent that stabilizes FVIII in the composition. Such agents are known to those of skill in the art, e.g., sucrose or albumin. The method can also be practiced by delivering to the cell a polynucleotide encoding the recombinant Factor VIII protein.

For the above noted methods, a non-limited example of a biological equivalent of recombinant Factor VIII, includes a fragment of recombinant Factor VIII, wherein the polypeptide can be, or alternatively is not in the form of a heterodimer and point mutated, substituted with an amino acid in at least 1 position, or alternatively at least 2 positions, or alternatively at least 3 positions, or alternatively at least 4 positions, or in all positions from the group consisting of Val120, Leu178, Ser1978, Glu2018, and Leu2020. Alternatively, additional chemical functional groups, capable of chelating copper or zinc, can be substituted onto existing amino acid side chains by post-translational modification. Such functionals include, but are not limited to: carboxylic acid, amine, amide, imine, guanidine, carbamate, porphyrin, chlorin, corrin, crown ether, cryptand, imidazole, pyrrole, piperidine, pyrrroldine, pyridine, thiol, sulfonic acid, sulfonate, and sulfamide.

The methods as described herein are particularly useful in the treatment of Hemophelia A and blotting clotting/coagulation diseases in general. Genetic mutation and insufficient expression of FVIII lead to Haemophelia A. Treatment replacing FVIII protein will restore FVIII expression and effectively increase FVIII half-life, FX activation, FIXa activation, thrombin activity, and ultimately increase blood coagulation. Therefore, the present invention is useful in the treatment of Hemophelia A and moreover in treatment where blood can act to heal or ameliorate injury.

Polypeptides

Applicant also provides an isolated or recombinant polypeptide comprising, or alternatively consisting essentially of, or yet further consisting of, recombinant FVIII protein point mutated, substituted with an amino acid in at least 1 position, or alternatively at least 2 positions, or alternatively at least 3 positions, or alternatively at least 4 positions, or in all positions from the group consisting of Val120, Leu178, Ser1978, Glu2018, and Leu2020, or a biological equivalent thereof. In one aspect, the polypeptide is not simply the wild-type FVIII protein in a mammalian cell system. The polypeptides can be recombinantly or chemically synthesized and can further comprise post-translational modification.

In another aspect, the isolated or recombinant polypeptide further comprises, or alternatively consists essentially of, or yet further consists of, an isolated or recombinant polypeptide including an agent that stabilizes FVIII in the composition. A non-limiting example of such is a polypeptide comprising, or alternatively consisting essentially of, or yet further consisting of, a composition including an isolated or recombinant polypeptide FVIII and albumin, or a biological equivalent thereof. Such agents are known to those of skill in the art, e.g., sucrose.

The isolated polypeptide as described herein may further comprise, or alternatively consist essentially of, or yet further consist of, at least one of a protein start site and/or a polyhistidine tag each operatively linked to the polypeptide.

The polypeptides can further comprise a detectable label. Such labels are known to those of skill in the art and examples of such are described herein.

An isolated host cell that comprises, or alternatively consists essentially of, or yet further consists of the isolated or recombinant polypeptide as described herein, is further provided. The isolated host cells can be a prokaryotic or a eukaryotic cell. Suitable cells containing the inventive polypeptides include prokaryotic and eukaryotic cells, which include, but are not limited to bacterial cells, algae cells, yeast cells, insect cells, plant cells, animal cells, mammalian cells, murine cells, rat cells, sheep cells, simian cells and human cells. A non-limiting example of algae cells is red alga *Griffithsia* sp. from (Toshiyuki et al. (2005) J. Biol. Chem. 280(10):9345-53). A non-limiting example of plant cells is a *Nicotiana benthamiana* leaf cell (O'Keefe (2009) Proc. Nat. Acad. Sci. USA 106(15):6099-6104). Examples of bacterial cells include *Escherichia coli* (Giomarelli et al. (2006), supra), *Salmonella enteric, Streptococcus gordonii* and *lactobacillus* (Liu et al. (2007) Cellular Microbiology 9:120-130; Rao et al. (2005) PNAS 102:11993-11998; Chang et al. (2003) PNAS 100(20):11672-11677; Liu et al. (2006) Antimicrob. Agents & Chemotherapy 50(10):3250-3259). The cells can be purchased from a commercial vendor such as the American Type Culture Collection (ATCC, Rockville Md., USA) or cultured from an isolate using methods known in the art. Examples of suitable eukaryotic cells include, but are not limited to 293T HEK cells, as well as the hamster cell line CHO, BHK-21; the murine cell lines designated NIH3T3, NS0, C127, the simian cell lines COS, Vero; and the human cell lines HeLa, PER.C6 (commercially available from Crucell) U-937 and Hep G2. A non-limiting example of insect cells include *Spodoptera frugiperda* and High Five cell-line (BTI-TN-5B1-4) derived from the ovarian cells of *Trichoplusia ni* (Granados, R. R., Guoxun, L., Derksen, A. C. G., and McKenna, K. A. (1994). A New Insect Cell Line from *Trichoplusia ni* (BTI-Tn-5B1-4) Susceptible to *Trichoplusia ni* Single Enveloped Nuclear Polyhedrosis. Virus. J. Invertebr. Pathol. 64, 260-266. Wickham, T. J., and Nemerow, G. R. (1993). Optimization of Growth Methods and Recombinant Protein Production in BTI Tn-5B1-4 Insect Cells using the Baculovirus Expression. Vector. Biotechnol. Prog. 9, 25-30. Examples of yeast useful for expression include, but are not limited to *Saccharomyces, Schizosaccharomyces, Hansenula, Candida, Torulopsis, Yarrowia,* or *Pichia*. See e.g., U.S. Pat. Nos. 4,812,405; 4,818,700; 4,929,555; 5,736,383; 5,955,349; 5,888,768 and 6,258,559.

Compositions are also provided. The compositions comprise, or alternatively consist essentially of, or yet further consist of, a carrier and the isolated or recombinant polypeptide as described herein. The carrier can be a solid support or a liquid carrier such as a pharmaceutically acceptable carrier.

Polypeptides comprising the recombinant Factor FVIII of the invention can be prepared by expressing polynucleotides encoding the polypeptide sequences of this invention in an appropriate host cell. This can be accomplished by methods of recombinant DNA technology known to those skilled in the art. Accordingly, this invention also provides methods for recombinantly producing the polypeptides of this invention in a eukaryotic or prokaryotic host cells, as well as the isolated host cells used to produce the proteins. The proteins and polypeptides of this invention also can be obtained by chemical synthesis using a commercially available automated peptide synthesizer such as those manufactured by Perkin Elmer/Applied Biosystems, Inc., Model 430A or 431A, Foster City, Calif., USA. The synthesized protein or polypeptide can be precipitated and further purified, for example by high performance liquid chromatography (HPLC). Accordingly, this invention also provides a process for chemically synthesizing the proteins of this invention by providing the sequence of the protein and reagents, such as amino acids and enzymes and linking together the amino acids in the proper orientation and linear sequence. The polypeptides can be chemically acetylated.

It is known to those skilled in the art that modifications can be made to any peptide to provide it with altered properties. Polypeptides of the invention can be modified to include one or more acetylated lysines and/or to unnatural amino acids. Thus, the peptides may comprise D-amino acids, a combination of D- and L-amino acids, and various "designer" amino acids (e.g., β-methyl amino acids, C-α-methyl amino acids, and N-α-methyl amino acids, etc.) to convey special properties to peptides. Additionally, by assigning specific amino acids at specific coupling steps, peptides with α-helices, β turns, β sheets, α-turns, and cyclic peptides can be generated. Generally, it is believed that α-helical secondary structure or random secondary structure is preferred.

In a further embodiment, subunits of polypeptides that confer useful chemical and structural properties will be chosen. For example, peptides comprising D-amino acids may be resistant to L-amino acid-specific proteases in vivo. Modified compounds with D-amino acids may be synthesized with the amino acids aligned in reverse order to produce the peptides of the invention as retro-inverso peptides. In addition, the present invention envisions preparing peptides that have better defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2NH$—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such molecules would provide ligands with unique function and activity, such as extended half-lives in vivo due to resistance to metabolic breakdown, or protease activity. Furthermore, it is well known that in certain systems constrained peptides show enhanced functional activity (Hruby (1982) Life Sciences 31:189-199 and Hruby et al. (1990) Biochem J. 268:249-262); the present invention provides a method to produce a constrained peptide that incorporates random sequences at all other positions.

Non-classical amino acids may be incorporated in the peptides of the invention in order to introduce particular conformational motifs, examples of which include without limitation: 1,2,3,4-tetrahydroisoquinoline-3-carboxylate (Kazmierski et al. (1991) J. Am. Chem. Soc. 113:2275-2283); (2S,3S)-methyl-phenylalanine, (2S,3R)-methyl-phenylalanine, (2R,3S)-methyl-phenylalanine and (2R,3R)-methyl-phenylalanine (Kazmierski & Hruby (1991) Tetrahedron Lett. 32(41):5769-5772); 2-aminotetrahydronaphthalene-2-carboxylic acid (Landis (1989) Ph.D. Thesis, University of Arizona); hydroxy-1,2,3,4-tetrahydroisoquinoline-3-carboxylate (Miyake et al. (1989) J. Takeda Res. Labs. 43:53-76) histidine isoquinoline carboxylic acid (Zechel et al. (1991) Int. J. Pep. Protein Res. 38(2):131-138); and HIC (histidine cyclic urea), (Dharanipragada et al. (1993) Int. J. Pep. Protein Res. 42(1):68-77) and (Dharanipragada et al. (1992) Acta. Crystallogr. C. 48:1239-1241).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog (Kemp et al. (1985) J. Org. Chem. 50:5834-5838); β-sheet inducing analogs (Kemp et al. (1988) Tetrahedron Lett. 29:5081-5082); β-turn inducing analogs (Kemp et al. (1988) Tetrahedron Lett. 29:5057-5060); α-helix inducing analogs (Kemp et al. (1988) Tetrahedron Lett. 29:4935-4938); α-turn inducing analogs (Kemp et al. (1989) J. Org. Chem. 54:109:115); analogs provided by the following references: Nagai & Sato (1985) Tetrahedron Lett. 26:647-650; and DiMaio et al. (1989) J. Chem. Soc. Perkin Trans. p. 1687; a Gly-Ala turn analog (Kahn et al. (1989) Tetrahedron Lett. 30:2317); amide bond isostere (Clones et al. (1988) Tetrahedron Lett. 29:3853-3856); tetrazole (Zabrocki et al. (1988) J. Am. Chem. Soc. 110:5875-5880); DTC (Samanen et al. (1990) Int. J. Protein Pep. Res. 35:501:509); and analogs taught in Olson et al. (1990) J. Am. Chem. Sci. 112:323-333 and Garvey et al. (1990) J. Org. Chem. 56:436. Conformationally restricted mimetics of beta turns and beta bulges, and peptides containing them, are described in U.S. Pat. No. 5,440,013, issued Aug. 8, 1995 to Kahn.

It is known to those skilled in the art that modifications can be made to any peptide by substituting one or more amino acids with one or more functionally equivalent amino acids that does not alter the biological function of the peptide. In one aspect, the amino acid that is substituted by an amino acid that possesses similar intrinsic properties including, but not limited to, hydrophobicity, size, or charge. Methods used to determine the appropriate amino acid to be substituted and for which amino acid are know to one of skill in the art. Non-limiting examples include empirical substitution models as described by Dahoff et al. (1978) In Atlas of Protein Sequence and Structure Vol. 5 suppl. 2 (ed. M. O. Dayhoff), pp. 345-352. National Biomedical Research Foundation, Washington D.C.; PAM matrices including Dayhoff matrices (Dahoff et al. (1978), supra, or JTT matrices as described by Jones et al. (1992) Comput. Appl. Biosci. 8:275-282 and Gonnet et al. (1992) Science 256:1443-1145; the empirical model described by Adach & Hasegawa (1996) J. Mol. Evol. 42:459-468; the block substitution matrices (BLOSUM) as described by Henikoff & Henikoff (1992) Proc. Natl. Acad. Sci. USA 89:1-1; Poisson models as described by Nei (1987) Molecular Evolutionary Genetics. Columbia University Press, New York.; and the Maximum Likelihood (ML) Method as described by Müller et al. (2002) Mol. Biol. Evol. 19:8-13.

Antibody Compositions

This invention also provides an antibody capable of specifically forming a complex with a polypeptide or polynucleotide of this invention, which are useful in the screens of this invention. The term "antibody" includes polyclonal antibodies and monoclonal antibodies, antibody fragments, as well anti-idiotypic, humanized, chimeric, and recombinant antibodies (described above). The antibodies include, but are not limited to mouse, rat, and rabbit or human antibodies. Antibodies can be produced in cell culture, in phage, or in various animals, including but not limited to cows, rabbits, goats, mice, rats, hamsters, guinea pigs, sheep, dogs, cats, monkeys, chimpanzees, apes, etc. The antibodies are also useful to identify and purify polypeptides.

This invention also provides an antibody-peptide complex comprising, or alternatively consisting essentially of, or yet alternatively consisting of, antibodies described above and a polypeptide or polynucleotide specifically bound to the antibody. In one aspect the polypeptide is the polypeptide against which the antibody was raised. In one aspect the antibody-peptide complex is an isolated complex. In a further aspect, the antibody of the complex is, but not limited to, a polyclonal antibody, a monoclonal antibody, an antibody fragment, a humanized antibody or an antibody derivative described herein. Either or both of the antibody or peptide of the antibody-peptide complex can be detectably labeled or further comprises a detectable label conjugated to it. In one aspect, the antibody-peptide complex of the invention can be used as a control or reference sample in diagnostic or screening assays.

Polyclonal antibodies of the invention can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, which induces the B-lymphocytes to produce IgG immunoglobulins specific for the antigen. This IgG is purified from the mammals serum. Variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antiben depot, which allows for a slow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods described in U.S. Pat. Nos. 7,279,559; 7,119,179; 7,060,800; 6,709,659; 6,656,746; 6,322,788; 5,686,073; and 5,670,153.

The monoclonal antibodies of the invention can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U397, MLA 144, ACT IV, MOLT4, DA-1, JURKAT, WEHI, K-562, COS, RAJI, NIH 3T3, HL-60, MLA 144, NAMAIWA, NEURO 2A, CHO, PerC.6, YB2/O) or the like, or heteromyelomas, fusion products thereof, or any cell or fusion cell derived therefrom, or any other suitable cell line as known in the art (see, e.g., www.atcc.org, www.lifetech.com., last accessed on Nov. 26, 2007, and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, preferably the spleen or lymph nodes, of humans or other suitable animals that have been immunized with the antigen of interest. Any other suitable host cell can also be used for expressing-heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods.

In one embodiment, the antibodies described herein can be generated using a Multiple Antigenic Peptide (MAP) system. The MAP system utilizes a peptidyl core of three or seven radially branched lysine residues, on to which the antigen peptides of interest can be built using standard solid-phase chemistry. The lysine core yields the MAP bearing about 4 to 8 copies of the peptide epitope depending on the inner core that generally accounts for less than 10% of total molecular weight. The MAP system does not require a carrier protein for conjugation. The high molar ratio and dense packing of multiple copies of the antigenic epitope in a MAP has been shown to produce strong immunogenic response. This method is described in U.S. Pat. No. 5,229,490 and is herein incorporated by reference in its entirety.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from various commercial vendors such as Cambridge Antibody Technologies (Cambridgeshire, UK), MorphoSys (Martinsried/Planegg, Del.), Biovation (Aberdeen, Scotland, UK) BioInvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1997) Microbiol. Immunol. 41:901-907; Sandhu et al. (1996) Crit. Rev. Biotechnol. 16:95-118; Eren et al. (1998) Immunol. 93:154-161 that are capable of producing a repertoire of human antibodies, as known in the art and/or as described herein. Such techniques, include, but are not limited to, ribosome display (Hanes et al. (1997) Proc. Natl. Acad. Sci. USA 94:4937-4942; Hanes et al. (1998) Proc. Natl. Acad. Sci. USA 95:14130-14135); single cell antibody producing technologies (e.g., selected lymphocyte antibody method ("SLAM") (U.S. Pat. No. 5,627,052, Wen et al. (1987) J. Immunol. 17:887-892; Babcook et al. (1196) Proc. Natl. Acad. Sci. USA 93:7843-7848); gel microdroplet and flow cytometry (Powell et al. (1990) Biotechnol. 8:333-337; One Cell Systems, (Cambridge, Mass.).; Gray et al. (1995) J. Imm. Meth. 182:155-163; and Kenny et al. (1995) Bio. Technol. 13:787-790); B-cell selection (Steenbakkers et al. (1994) Molec. Biol. Reports 19:125-134.

Antibody derivatives of the present invention can also be prepared by delivering a polynucleotide encoding an antibody of this invention to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

The term "antibody derivative" also includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fc-mediated cellular toxicity, and glycoproteins so generated.

Antibody derivatives also can be prepared by delivering a polynucleotide of this invention to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody derivatives have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and reference cited therein. Thus, antibodies of the present invention can also be produced using transgenic plants, according to know methods.

Antibody derivatives also can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

In general, the CDR residues are directly and most substantially involved in influencing antigen binding. Humanization or engineering of antibodies of the present invention can be performed using any known method such as, but not limited to, those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See for example, Russel et al. (2000) Infection and Immunity April 68(4):1820-1826; Gallo et al. (2000) European J. of Immun. 30:534-540; Green (1999) J. of Immun. Methods 231:11-23; Yang et al. (1999A) J. of Leukocyte Biology 66:401-410; Yang (1999B) Cancer Research 59(6):1236-1243; Jakobovits (1998) Advanced Drug Delivery Reviews 31:33-42; Green & Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold (1997) Genetic Engineering News 17(14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al. (1995) Genomics 26:294-307; Jakobovits (1994) Current Biology 4(8):761-763; Arbones et al. (1994) Immunity 1(4):247-260; Jakobovits (1993) Nature 362(6417): 255-258; Jakobovits et al. (1993) Proc. Natl. Acad. Sci. USA 90(6):2551-2555; and U.S. Pat. No. 6,075,181.)

The antibodies of this invention also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, the antibodies of this invention can also be modified to create veneered antibodies. Veneered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in another mammalian species antibodies. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Kabat et al. (1987) Sequences of Proteins of Immunological Interest, 4th ed., Bethesda, Md., National Institutes of Health, updates to this database, and other accessible U.S. and foreign databases (both nucleic acid and protein). Non-limiting examples of the methods used to generate veneered antibodies include EP 519596; U.S. Pat. No. 6,797,492; and described in Padlan et al. (1991) Mol. Immunol. 28(4-5):489-498.

The term "antibody derivative" also includes "diabodies" which are small antibody fragments with two antigen-binding sites, wherein fragments comprise a heavy chain variable domain (VH) connected to a light chain variable domain (VL) in the same polypeptide chain. (See for example, EP 404,097; WO 93/11161; and Hollinger et al. (1993) Proc. Natl. Acad. Sci. USA 90:6444-6448.) By using a linker that is too short to allow pairing between the two domains on the same chain, the domains are forced to pair with the complementary domains of another chain and create two antigen-binding sites. (See also, U.S. Pat. No. 6,632,926 to Chen et al. which discloses antibody variants that have one or more amino acids inserted into a hypervariable region of the parent antibody and a binding affinity for a target antigen which is at least about two fold stronger than the binding affinity of the parent antibody for the antigen.)

The term "antibody derivative" further includes "linear antibodies". The procedure for making linear antibodies is known in the art and described in Zapata et al. (1995) Protein Eng. 8(10):1057-1062. Briefly, these antibodies comprise a pair of tandem Fd segments ($V_H$-$C_H$1-VH-$C_H$1) which form a pair of antigen binding regions. Linear antibodies can be bispecific or monospecific.

The antibodies of this invention can be recovered and purified from recombinant cell cultures by known methods including, but not limited to, protein A purification, ammonium sulfate or ethanol precipitation, acid extraction, ion exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present invention include naturally purified products, products of chemical synthetic procedures, and products produced by recombinant techniques from a eukaryotic host, including, for example, yeast, higher plant, insect and mammalian cells, or alternatively from a prokaryotic cells as described above.

If a monoclonal antibody being tested binds with protein or polypeptide, then the antibody being tested and the antibodies provided by the hybridomas of this invention are equivalent. It also is possible to determine without undue experimentation, whether an antibody has the same specificity as the monoclonal antibody of this invention by determining whether the antibody being tested prevents a monoclonal antibody of this invention from binding the protein or polypeptide with which the monoclonal antibody is normally reactive. If the antibody being tested competes with the monoclonal antibody of the invention as shown by a decrease in binding by the monoclonal antibody of this invention, then it is likely that the two antibodies bind to the same or a closely related epitope. Alternatively, one can pre-incubate the monoclonal antibody of this invention with a protein with which it is normally reactive, and determine if the monoclonal antibody being tested is inhibited in its ability to bind the antigen. If the monoclonal antibody being tested is inhibited then, in all likelihood, it has the same, or a closely related, epitopic specificity as the monoclonal antibody of this invention.

The term "antibody" also is intended to include antibodies of all isotypes. Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski, et al. (1985) Proc. Natl. Acad. Sci. USA 82:8653 or Spira et al. (1984) J. Immunol. Methods 74:307.

The isolation of other hybridomas secreting monoclonal antibodies with the specificity of the monoclonal antibodies of the invention can also be accomplished by one of ordinary skill in the art by producing anti-idiotypic antibodies. Herlyn et al. (1986) Science 232:100. An anti-idiotypic antibody is an antibody which recognizes unique determinants present on the monoclonal antibody produced by the hybridoma of interest.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the mirror image of the epitope bound by the first monoclonal antibody. Thus, in this instance, the anti-idiotypic monoclonal antibody could be used for immunization for production of these antibodies.

In some aspects of this invention, it will be useful to detectably or therapeutically label the antibody. Suitable labels are described supra. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample.

The coupling of antibodies to low molecular weight haptens can increase the sensitivity of the antibody in an assay. The haptens can then be specifically detected by means of a second reaction. For example, it is common to use haptens such as biotin, which reacts avidin, or dinitrophenol, pyridoxal, and fluorescein, which can react with specific anti-hapten antibodies. See, Harlow & Lane (1988) supra.

The antibodies of the invention also can be bound to many different carriers. Thus, this invention also provides compositions containing the antibodies and another substance, active or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

Isolated or Recombinant Polynucleotides

Further provided is an isolated or recombinant polynucleotide encoding the isolated polypeptide or an interfering polynucleotide as described above as well as a vector or other polynucleotide construct comprising a delivery vehicle or vector and a polynucleotide of this invention. Non-limiting examples of delivery vehicles include a plasmid, a yeast artificial chromosome, a liposome, a micelle, or a viral vector.

This invention further provides isolated or recombinant polynucleotides that encode the polypeptides of this invention or for use in the methods of this invention as well as isolated or recombinant polynucleotides that bind to and inhibit the expression of these polynucleotides such as agents for effecting RNA interference (RNAi) such as dsRNA, miRNA, siRNA, shRNA and antisense RNA. Yet another aspect of the invention provides an isolated polynucleotide encoding for an antibody or a fragment of the antibody of the invention.

The isolated polynucleotides can further comprise, or alternatively consist essentially of, or yet further consist of regulatory polynucleotide sequences operatively linked to the isolated polynucleotide. The isolated polynucleotides can be inserted into an expression or delivery vehicle or an isolated host cell. The host cells can be used to recombinantly produce the polypeptides by growing the host cell containing an isolated polynucleotide under conditions that favor the expression of the isolated polynucleotide. In one aspect, the polypeptide produced from the polynucleotide is isolated from the host cell. Also provided is a DNA construct comprising an expression or delivery vehicle and a polynucleotide. In one aspect, the vector is a plasmid vector, a yeast artificial chromosome, or a viral vector. In one aspect, the vector comprises a protein tag. Protein tags can be selected from a GST-tag, a myc-tag, or a FLAG-tag provided in expression constructs commercially available from, e.g., Invitrogen, Carlbad, Calif.

Another aspect of the invention provides an isolated host cell transformed with a polynucleotide or a DNA construct of the invention. The isolated host cells can be a prokaryotic or a eukaryotic cell. Yet another aspect of the invention provides an isolated transformed host cell expressing an isolated polypeptide, an antibody or a fragment of the antibody of the invention. The isolated host cells can be a prokaryotic or a eukaryotic cell. Suitable cells containing the inventive polypeptides include prokaryotic and eukaryotic cells, which include, but are not limited to bacterial cells, algae cells, yeast cells, insect cells, plant cells, animal cells, mammalian cells, murine cells, rat cells, sheep cells, simian cells and human cells. A non-limiting example of algae cells is red alga *Griffithsia* sp. from (Toshiyuki et al. (2005) J. Biol. Chem. 280(10):9345-53). A non-limiting example of plant cells is a *Nicotiana benthamiana* leaf cell (O'Keefe (2009) Proc. Nat. Acad. Sci. USA 106(15):6099-6104). Examples of bacterial cells include *Escherichia coli* (Giomarelli et al. (2006), supra), *Salmonella enteric*, *Streptococcus gordonii* and *lactobacillus* (Liu et al. (2007) Cellular Microbiology 9:120-130; Rao et al. (2005) PNAS 102:11993-11998; Chang et al. (2003) PNAS 100(20): 11672-11677; Liu et al. (2006) Antimicrob. Agents & Chemotherapy 50(10):3250-3259). The cells can be purchased from a commercial vendor such as the American Type Culture Collection (ATCC, Rockville Md., USA) or cultured from an isolate using methods known in the art. Examples of suitable eukaryotic cells include, but are not limited to 293T HEK cells, as well as the hamster cell line CHO, BHK-21; the murine cell lines designated NIH3T3, NS0, C127, the simian cell lines COS, Vero; and the human cell lines HeLa, PER.C6 (commercially available from Crucell) U-937 and Hep G2. A non-limiting example of insect cells include *Spodoptera frugiperda* and High Five cell-line (BTI-TN-5B1-4) derived from the ovarian cells of *Trichoplusia ni* (Granados, R. R., Guoxun, L., Derksen, A. C. G., and McKenna, K. A. (1994). A New Insect Cell Line from *Trichoplusia ni* (BTI-Tn-5B1-4) Susceptible to *Trichoplusia ni* Single Enveloped Nuclear Polyhedrosis. Virus. J. Invertebr. Pathol. 64, 260-266. Wickham, T. J., and Nemerow, G. R. (1993). Optimization of Growth Methods and Recombinant Protein Production in BTI Tn-5B1-4 Insect Cells using the Baculovirus Expression. Vector. Biotechnol. Prog. 9, 25-30. Examples of yeast useful for expression include, but are not limited to *Saccharomyces, Schizosaccharomyces, Hansenula, Candida, Torulopsis, Yarrowia,* or *Pichia.* See e.g., U.S. Pat. Nos. 4,812,405; 4,818,700; 4,929,555; 5,736,383; 5,955,349; 5,888,768 and 6,258,559.

Also provided are polynucleotides encoding substantially homologous and biologically equivalent polypeptides to the inventive polypeptides and polypeptide complexes. Substantially homologous and biologically equivalent intends those having varying degrees of homology, as described above. It should be understood although not always explicitly stated that embodiments to substantially homologous polypeptides and polynucleotides are intended for each aspect of this invention, e.g., polypeptides, polynucleotides and antibodies.

The polynucleotides of this invention can be replicated using conventional recombinant techniques. Alternatively, the polynucleotides can be replicated using PCR technology. PCR is the subject matter of U.S. Pat. Nos. 4,683,195; 4,800,159; 4,754,065; and 4,683,202 and described in PCR: The Polymerase Chain Reaction (Mullis et al. eds, Birkhauser Press, Boston (1994)) and references cited therein. Yet further, one of skill in the art can use the sequences provided herein and a commercial DNA synthesizer to replicate the DNA. Accordingly, this invention also provides a process for obtaining the polynucleotides of this invention by providing the linear sequence of the polynucleotide, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can operatively link the polynucleotides to regulatory sequences for their expression in a host cell. The polynucleotides and regulatory sequences are inserted into the host cell (prokaryotic or eukaryotic) for replication and amplification. The DNA so amplified can be isolated from the cell by methods well known to those of skill in the art. A process for obtaining polynucleotides by this method is further provided herein as well as the polynucleotides so obtained.

The polynucelotides can be detectably labeled.

Host Cells and Compositions

Also provided by this invention is one or more of an isolated or recombinant polypeptide, an antibody, or an isolated or recombinant polynucleotide or host cell further comprising a detectable label as described above. Non-limiting examples of detectable labels include a protein, an enzyme, a protein tag, or a radioisotope.

Any of the above noted polypeptide, polynucleotide, antibody or host cell can be further combined with a carrier, excipient, or diluent. In one aspect, the carrier, excipient, or diluent is pharmaceutically acceptable. The carrier can be a solid phase carrier, a gel, an aqueous liquid carrier, a paste, a liposome, a micelle, albumin, polyethylene glycol, a pharmaceutically acceptable polymer, or a pharmaceutically acceptable carrier, such a phosphate buffered saline.

The compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, injections, emulsions, elixirs, suspensions or solutions. Compositions may optionally contain stabilizers, pH modifiers, surfactants, bioavailability modifiers and combinations of these.

Compositions may be prepared as liquid suspensions or solutions using a sterile liquid, such as oil, water, alcohol, and combinations thereof. Pharmaceutically suitable surfactants, suspending agents or emulsifying agents, may be added for oral or parenteral administration. Suspensions may include oils, such as peanut oil, sesame oil, cottonseed oil, corn oil and olive oil. Suspension preparation may also contain esters of fatty acids, such as ethyl oleate, isopropyl myristate, fatty acid glycerides and acetylated fatty acid glycerides. Suspension compositions may include alcohols, such as ethanol, isopropyl alcohol, hexadecyl alcohol, glycerol and propylene glycol. Ethers, such as poly(ethyleneglycol), petroleum hydrocarbons, such as mineral oil and petrolatum, and water may also be used in suspension compositions.

The compositions of this invention are formulated for pharmaceutical administration to a mammal, preferably a human being. Such compositions of the invention may be administered in a variety of ways, preferably topically or by injection. Such compositions may also be administered by way of catheter, i.v. infusion, or any general method known in the art that is applicable toward the circulatory system.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

In addition to dosage forms described above, pharmaceutically acceptable excipients and carriers and dosage forms are generally known to those skilled in the art and are included in the invention. It should be understood that a specific dosage and treatment regimen for any particular subject will depend upon a variety of factors, including the activity of the specific antidote employed, the age, body weight, general health, sex and diet, renal and hepatic function of the subject, and the time of administration, rate of excretion, drug combination, judgment of the treating physician or veterinarian and severity of the particular disease being treated.

Another aspect of the invention provides a peptide conjugate comprising, or alternatively consisting essentially of, or alternatively consisting of, a carrier covalently or non-covalently linked to an isolated polypeptide of the invention.

In some embodiments, the carrier comprises a liposome, or alternatively a micelle, or alternatively a pharmaceutically acceptable polymer, or a pharmaceutically acceptable carrier.

The polypeptides and polypeptide conjugates of the invention can be used in a variety of formulations, which may vary depending on the intended use. For example, one or more can be covalently or non-covalently linked (complexed) to various other molecules, the nature of which may vary depending on the particular purpose. For example, a peptide of the invention can be covalently or non-covalently complexed to a macromolecular carrier, including, but not limited to, natural and synthetic polymers, proteins, polysaccharides, polypeptides (amino acids), polyvinyl alcohol, polyvinyl pyrrolidone, and lipids. A peptide can be conjugated to a fatty acid, for introduction into a liposome, see U.S. Pat. No. 5,837,249. A peptide of the invention can be complexed covalently or non-covalently with a solid support, a variety of which are known in the art and described herein. An antigenic peptide epitope of the invention can be associated with an antigen-presenting matrix such as an MHC complex with or without co-stimulatory molecules.

Examples of protein carriers include, but are not limited to, superantigens, serum albumin, tetanus toxoid, ovalbumin, thyroglobulin, myoglobulin, and immunoglobulin.

Peptide-protein carrier polymers may be formed using conventional cross-linking agents such as carbodimides. Examples of carbodimides are 1-cyclohexyl-3-(2-morpholinyl-(4-ethyl) carbodiimide (CMC), 1-ethyl-3-(3-dimethylaminopropyl) carbodiimide (EDC) and 1-ethyl-3-(4-azonia-44-dimethylpentyl) carbodiimide.

Examples of other suitable cross-linking agents are cyanogen bromide, glutaraldehyde and succinic anhydride. In general, any of a number of homo-bifunctional agents including a homo-bifunctional aldehyde, a homo-bifunctional epoxide, a homo-bifunctional imido-ester, a homo-bifunctional N-hydroxysuccinimide ester, a homo-bifunctional maleimide, a homo-bifunctional alkyl halide, a homo-bifunctional pyridyl disulfide, a homo-bifunctional aryl halide, a homo-bifunctional hydrazide, a homo-bifunctional diazonium derivative, a chelating metal ion such as silver or copper or zinc, and even a homo-bifunctional photoreactive compound may be used. Also included are hetero-bifunctional compounds, for example, compounds having an amine-reactive and a sulfhydryl-reactive group, compounds with an amine-reactive and a photoreactive group and compounds with a carbonyl-reactive and a sulfhydryl-reactive group.

Specific examples of such homo-bifunctional cross-linking agents include the bifunctional N-hydroxysuccinimide esters dithiobis(succinimidylpropionate), disuccinimidyl suberate, and disuccinimidyl tartrate; the bifunctional imido-esters dimethyl adipimidate, dimethyl pimelimidate, and dimethyl suberimidate; the bifunctional sulfhydryl-reactive crosslinkers 1,4-di-[3'-(2'-pyridyldithio) propionamido]butane, bismaleimidohexane, and bis-N-maleimido-1,8-octane; the bifunctional aryl halides 1,5-difluoro-2,4-dinitrobenzene and 4,4'-difluoro-3,3'-dinitrophenylsulfone; bifunctional photoreactive agents such as bis-[b-(4-azidosalicylamido)ethyl]disulfide; the bifunctional aldehydes formaldehyde, malondialdehyde, succinaldehyde, glutaraldehyde, and adipaldehyde; a bifunctional epoxide such as 1,4-butaneodiol diglycidyl ether; the bifunctional hydrazides adipic acid dihydrazide, carbohydrazide, and succinic acid dihydrazide; the bifunctional diazoniums o-tolidine, diazotized and bis-diazotized benzidine; the bifunctional alkylhalides N1N'-ethylene-bis(iodoacetamide), N1N'-hexamethylene-bis(iodoacetamide), N1N'-undecamethylene-bis(iodoacetamide), as well as benzylhalides and halomustards, such as a1a'-diiodo-p-xylene sulfonic acid and tri(2-chloroethyl)amine, respectively.

Examples of common hetero-bifunctional cross-linking agents that may be used to effect the conjugation of proteins to peptides include, but are not limited to, SMCC (succinimidyl-4-(N-maleimidomethyl)cyclohexane-1-carboxylate), MBS (m-maleimidobenzoyl-N-hydroxysuccinimide ester), SIAB (N-succinimidyl(4-iodoacteyl)aminobenzoate), SMPB (succinimidyl-4-(p-maleimidophenyl) butyrate), GMBS (N-(γ-maleimidobutyryloxy)succinimide ester), MPBH (4-(4-N-maleimidopohenyl) butyric acid hydrazide), M2C2H (4-(N-maleimidomethyl) cyclohexane-1-carboxyl-hydrazide), SMPT (succinimidyloxycarbonyl-α-methyl-α-(2-pyridyldithio)toluene), and SPDP (N-succinimidyl 3-(2-pyridyldithio)propionate).

Cross-linking may be accomplished by coupling a carbonyl group to an amine group or to a hydrazide group by reductive amination.

The polypeptides or polynucleotides of the compositions of the invention also may be formulated as non-covalent attachment of monomers through ionic, adsorptive, or biospecific interactions. Complexes of peptides with highly positively or negatively charged molecules may be done through salt bridge formation under low ionic strength environments, such as in deionized water. Large complexes can be created using charged polymers such as poly-(L-glutamic acid) or poly-(L-lysine) which contain numerous negative and positive charges, respectively. Adsorption of peptides may be done to surfaces such as microparticle latex beads or to other hydrophobic polymers, forming non-covalently associated peptide-superantigen complexes effectively mimicking cross-linked or chemically polymerized protein. Finally, peptides may be non-covalently linked through the use of biospecific interactions between other molecules. For instance, utilization of the strong affinity of biotin for proteins such as avidin or streptavidin or their derivatives could be used to form peptide complexes. These biotin-binding proteins contain four binding sites that can interact with biotin in solution or be covalently attached to another molecule. (See Wilchek (1988) Anal. Biochem. 171:1-32). Peptides can be modified to possess biotin groups using common biotinylation reagents such as the N-hydroxysuccinimidyl ester of D-biotin (NHS-biotin) which reacts with available amine groups on the protein. Biotinylated peptides then can be incubated with avidin or streptavidin to create large complexes. The molecular mass of such polymers can be regulated through careful control of the molar ratio of biotinylated peptide to avidin or streptavidin.

Kits

An aspect of the invention provides a kit for detecting the impairment of proteolytic degradation of Factor VIII protein in the circulatory system. In one aspect, the invention provides a kit for use in detecting an increase in thrombin, FX, and/or FIXa activity in a eukaryotic cell comprising, or alternatively consisting essentially of, or alternatively consisting of, one or more of an isolated or recombinant polypeptide, an isolated or recombinant polynucleotide or an antibody of the invention and instructions to use.

Also provided is a kit for use in treating a subject in need thereof, comprising, or alternatively consisting essentially of, or alternatively consisting of, an isolated or recombinant polypeptide or polynucleotide or a composition of the invention, and instructions to use.

Kits may further comprise suitable packaging and/or instructions for use of the compositions. The compositions can be in a dry or lyophilized form, in a solution, particularly a sterile solution, or in a gel or cream. The kit may contain a device for administration or for dispensing the compositions, including, but not limited to, syringe, pepitte, transdermal patch and/or microneedle.

The kits may include other therapeutic compounds for use in conjunction with the compounds described herein. These compounds can be provided in a separate form or mixed with the compounds of the present invention.

The kits will include appropriate instructions for preparation and administration of the composition, side effects of the compositions, and any other relevant information. The instructions can be in any suitable format, including, but not limited to, printed matter, videotape, computer readable disk, or optical disc.

In another aspect of the invention, kits for treating a subject who suffers from or is susceptible to the conditions described herein are provided, comprising a container comprising a dosage amount of a composition as disclosed herein, and instructions for use. The container can be any of those known in the art and appropriate for storage and delivery.

Kits may also be provided that contain sufficient dosages of the effective composition or compound to provide effective treatment for a subject for an extended period, such as a week, 2 weeks, 3, weeks, 4 weeks, 6 weeks, or 8 weeks or more.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

General Experimental Overview

Among various modifications, point mutagenesis at as many as five distinct amino acid positions will provide recombinant FVIII protein capable of chelating copper or zinc ions at the A1-A3 domain interface. Such interaction stabilizes the recombinant protein.

The present invention having been described by figures, in summary, and in detail, is illustrated and not limited by the following example that includes within itself a number of exemplary, non-limiting compositions and methods.

Abbreviations

CP—Ceroplasmin
hCP—human Ceroplasmin
FVIII—Factor VIII protein
hFVIII—human Factor VIII protein
His—Histidine
Val—Valine Leu—Leucine
Ser—Serine
Glu—Glutamic acid
Min—minutes
g—grams
L—liters
h—hours
m—mili
ml—milliliters
w—weight
v—volume
n—nano
nm—nanometer
cm—centimeter
C—Centigrade
M—molar
mM—milimolar
µ—micro
µM—micromolar
HC—heavy chain
LC—light chain
ELISA—enzyme-linked immunosorbent assay
SDS-PAGE—sodium dodecyl sulfate polyacrylamide gel electrophoresis Example 1

Materials and Methods

Site Directed Mutagenesis

Multiple amino acid sequence alignment reveal two Histidine ligands (His118 and His1976) coordinating Type II copper are conserved in hFVIII sequence, while only one (His180) out of six His ligands involved in organizing two Type III copper binding is conserved. The remaining five are non-coordinating Val120, Leu178, Ser1978, Glu2018, and Leu2020 residues. These residues are highlighted red in Table 2. Substitution of all five residues to an amino acide capable of chelating copper or zinc ions was accomplished by site directed mutagenesis on the template of pFastBac-hF8BDRfugu plasmid. Close examination of hCP and hFVIII structures and their superimposition at the trinuclear copper site reveal an evenly matched similarity in the layout of side-chains of five amino acid targets for mutagenesis in hFVIII with analogous Histidine residues in hCP. It is known in the art that independent X-ray crystallographic studies have revealed no copper bound to the Type II site in wild-type human FVIII. Mutagenesis was performed by the use of a modified kit recently developed by Agilent (QuikChange Lightning Multi Site-Directed Mutagenesis Kit, Cat. #210513) or by New England Biolabs (Q5 Site-Directed Mutagenesis Kit, Cat. #E0554S). Final quintuple mutant was used for recombinant bacmid construction, packaging into baculovirus and protein expression.

Protein Expression and Purification

Protein expression was carried out using established protocols well known in the art. Invitrogen High Five cells gave good yield (~30 µg/ml of secreted protein). Protein were expressed in High Five cells in batches of 4×1 L suspension culture for 42 hours post-infection and centrifuged for 15-20 minutes to remove cell debris. Purification was affected after ethanol-fractionation from plasma and a single step of anion-exchange chromatography followed by precipitation with ammonium sulfate. Recovery from an ammonium sulfate precipitate, even after over a several months storage at −20° C., produced high quality protein. The cell culture media containing expressed FVIII protein was centrifuged to remove cell debris and buffered with 50 mM Tris-buffer, pH 7.4. A 1 ml aliquot of the clear supernatant from each 1 L flask was kept for further analyses of the expression efficiency by Western blot. The protein was immediately precipitated by ammonium sulfate, which was carried out at 27° C. using fine powder of ammonium sulfate crystals ground in an agate mortar. To achieve ~60% saturation, ~394 g (adjusted to compensate ~0.54 ml of volume increase per gram of dissolved salt) of fine powder of ammonium sulfate crystals per 1 L of supernatant from expression media will be gradually dissolved. The solution was left over night for proper precipitate formation and the protein precipitate was collected by centrifugation at 10,000 g for 30 min at 27° C. The precipitates were stored at −20° C. until Western blot analyzes confirmed the expression efficiency. For final purification of the protein, a combination of anion exchange and gelfiltration chromatography was used. Ammonium sulfate pellets from successful expression batches were pooled together and gradually resuspended in a 50-fold volume (with respect to the pellet volume) of 20 mM Tris buffer, pH7.4 containing 1 mM $CaCl_2$, and 0.5 µM of each $CuCl_2$ and $ZnCl_2$. Precipitate is formed during this step and was removed by centrifugation and the clear supernatant subjected to ultrafiltration in 400 ml Amicon Stirred Cells using YM-30 membrane (Millipore, Cat #13742.) Three rounds of dilution and concentration was performed to bring the ionic strength of the protein solution suitable for anion-exchanged chromatography on Whatman diethylaminoethyl (DEAE) cellulose (DE-52, Cat #4057-200). The isoelectric points of the single chain, full-length protein were estimated to be ~6.0, while for light chain, B-domain free heavy chain, and fugu B-domain alone are 5.7, 7.7, and 4.8, respectively. The protein was eluted from the column by a linear gradient of increasing ionic strength from 20 mM to 200 mM using 1M NaCl solution in the same buffer (20 mM Tris, pH7.4, 1 mM $CaCl_2$, 0.5 µM $CuCl_2$, 0.5 µM $ZnCl_2$). Free, uncomplexed, heavy or light chains were identified in the protein fractions and were separated from the SC and LC/HC complex during size exclusion chromatography stage of purification. Western blot or ELISA was used to identify FVIII protein were pooled together, concentrated to an appropriate volume and applied to the size-exclusion chromatography on Sephacryl S-300 column (GE Healthcare Life Sciences, Cat #17-0599-01). After analyzing by coomassie stained SDS-PAGE and Western blot homogeneous fractions were subjected to metal analyzes, and tested for activity. For samples displaying highest activity, thermodynamic parameters of the protein unfolding were calculated using differential scanning calorimetry. For long term storage the protein samples were transferred to a stabilizing solution formulated by manufacturers of Advate (Baxter), Cogenate (Bayer) or Xynta (Pfizer.) To the 20 mM Tris, pH7.4, buffer 350 mM NaCl, 2 mM $CaCl_2$, 0.5 µM of each $CuCl_2$ and $ZnCl_2$, 6% Mannitol, 2% (w/v) α,α Trehalose, and 0.02% Polysorbate 80 were added and stored at −70° C.

FVIII Activity Assay

FVIII activity measurement will be carried out using in-house modified version of Coatest SP FVIII (Chromogenix, Instrumentation Laboratory Company, North America, Bedford, Mass. Cat #82408663) chromogenic kit so that allowed more flexibility in changing reaction conditions when needed. The SC FVIII or LC/HC heterodimer (~0.5 to 1 nM) was activated in advance with 30 nM of α-thrombin in 25 mM HEPES, buffer, pH7.2, containing 100 mM NaCl, 5 mM $CaCl_2$, 0.1 mg/mL BSA, and 20 µM phospholipid vesicles. The reaction was terminated after 1-2 min by addition of 25 units/mL thrombin inhibitor, hirudin. To the FVIIIa solution 10 nM of FIXa and 0.5 mM of chromogenic substrate S-2765, N-α-Z-D-Arg-Gly-Arg-pNA.2HCl (N,α-benzyloxycarbonyl-D-arginyl-glycyl-L-arginyl-4-nitroanilide-dihydrochloride, Instrumentation Laboratory Company, North America, Bedford, Mass.) was added. The reaction wase initiated by addition of 500 nM of FX to the tenase complex. This solution was gently mixed by pipetting up and down inside the spectrophotometric cuvette and the progression of para-nitroaniline formation was monitored at 405 nm using a UV-Vis spectrophotometer tuned for fixed, single-wavelength kinetic measurements. Initial velocities were calculated using early, linear phase of kinetic curve. The reference cuvette contained all components of the reaction mixture, save FX. All reactions were carried out in a room air-conditioned at ~25° C. Factor X, Factor IXa, and α-thrombin were purchased from Enzyme Research Laboratories, South Bend, Ind. (cat #HFX 1010, HFIXa 1080 and HT 1002a, respectively). Phosphatidylcholine (PC) and Phosphatidylserine (PS) were used as lipid components at PC/PS ratio of 3:1 for lipid vesicle formation. For soluble lipid vesicle preparation, detergent (N-octylglucoside) induced solubilization technique was used at 3:1 detergent/lipid ratio. All components of the reaction mixture save soluble lipid vesicle (to avoid possible Cu mediated peroxidation) for activity measurement also contained $CuCl_2$ and $ZnCl_2$ each at concentrations adjusted so that the final mixture had at least 0.5 μM of each $CuCl_2$ and $ZnCl_2$.

Metal Ion and Thermal Stability Analyses by ICP-MS & DSC

Metal ion quantitation analyses will be carried out using ICP-MS (inductively coupled plasma mass spectrometry) instruments at UCLA Pasarow Mass Spectrometry Laboratory (long-term research collaboration). Prior to sample analysis, careful review of the calibration curve is needed to be carried out with respect to percent relative standard deviation (% RSD), correlation (r2), and two quality control samples, which were analyzed against the calibration curve. Protein samples were analyzed only after these parameters are checked and found to be valid. The concentration of purified protein samples were calculated using molar extinction coefficient, ~260,000 $M^{-1}$ $cm^1$, for the optical absorption band at 280 nm. This value for ε280 is estimated based on Trp (28residues) and Tyr (71residues) content in the SC variant. Nitric acid was added (5% final concentration) to 1-2 ml of ~4 μM (~1 mg/ml) protein solution and analyzed on an ICP-MS instrument optimized and wavelengths calibrated for Cu, Zn, and Ca to allow simultaneous determination of these metals at lowest possible detection limits at 4 nM, 10 nM, and 30 nM for Cu, Zn, and Ca, respectively. Thermal stabilities of proteins were determined by Differential Scanning calorimetry (DSC). carried out on a Nano II differential scanning calorimeter (Calorimetry Sciences Corp.). The Nano II differential scanning calorimeter was equipped with U-shaped reference cell and a sample cell. In all DSC experiments, the sample cell was filled with 326.8 μl of 1.5 to 2 mg/ml protein solution in the same buffer used to fill the reference cell. To avoid air bubble formation during heating, all buffer and protein solutions were extensively degassed for 15 min by a water aspirator generated vacuum. A buffer versus buffer base-line was measured prior to the calorimetric analysis of protein samples. All samples were run in duplicate through a temperature range of 25-90° C. at a rate of 1° C./min under 3 atm of pressure. CpCalc software (Calorimetry Sciences Corp.) was used to determine molar heat capacity values, and Origin software (Microcal) was used to fit the data to an appropriate thermal transition model. Orotein samples were sent to X-ray crystallography core laboratory at University of Texas Health Science Center, San Antonio for crystallization trials and further X-ray structure determination.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A biologically active, recombinant factor VIII polypeptide comprising the amino acid sequence of wild-type human FVIII protein or wherein the biologically active, recombinant factor VIII (FVIII) polypeptide is modified from the B domain and possesses an amino acid sequence having at least 90% sequence identity to a wild-type human FVIII protein;

wherein said sequence has been modified by substitution at one or more residues selected from the group consisting of Val120, Leu178, Ser1978, Glu2018, and Leu2020 with a copper or zinc ion chelating amino acid such that the biologically active recombinant factor VIII polypeptide chelates at least two copper or zinc ions.

2. The recombinant FVIII polypeptide of claim 1, which is capable to chelate at least three copper or zinc cations.

3. The recombinant FVIII polypeptide of claim 1, comprising amino acid substitution at two or more residues selected from the group consisting of Val120, Leu178, Ser1978, Glu2018, and Leu2020.

4. The recombinant FVIII polypeptide of claim 1, comprising amino acid substitution for all residues of Val120, Leu178, Ser1978, Glu2018, and Leu2020.

5. The recombinant FVIII polypeptide of claim 1, wherein the amino acid substitution is substitution with an amino acid selected from the group consisting of histidine, lysine, cysteine, methionine, proline, tryptophan, tyrosine, arginine, asparagine, glutamine, aspartic acid, and glutamic acid.

6. The recombinant FVIII polypeptide of claim 1, wherein the amino acid substitution is substitution with histidine.

7. The recombinant FVIII polypeptide of claim 1, wherein the polypeptide is post-translationally modified with an organic functional group that chelates at least one copper or zinc ion.

8. The recombinant FVIII polypeptide of claim 1, wherein the substitution is with an amino acid derivative that is functionalized with a nucleobase or an organic functional group selected from the group consisting of carboxylic acid, amine, amide, imine, guanidine, carbamate, porphyrin, chlorin, corrin, crown ether, cryptand, imidazole, pyrrole, piperidine, pyrrolidone, pyridine, thiol, sulfonic acid, sulfonate, and sulfamide or a functional group that reacts under physiological conditions in order to form said organic functional groups.

9. The recombinant FVIII polypeptide of claim 1, wherein the polypeptide is modified from the B domain and possesses an amino acid sequence having at least 95% to that of the wild-type FVIII protein.

10. A biologically, recombinant factor VIII (FVIII) polypeptide comprising the amino acid sequence of wild-type human FVIII protein, which does not include a B domain;

wherein said sequence has been modified by substitution at one or more residues selected from the group consisting of Val120, Leu178, Ser1978, Glu2018, and Leu2020 with a copper or zinc ion chelating amino acid such that the biologically active recombinant factor VIII polypeptide chelates at least two copper or zinc ions.

11. Synthetic blood comprising the recombinant FVIII polypeptide of claim 1.

12. A method for enhancing or restoring blood coagulation in a patient suffering from a coagulation disease, comprising administering to the patient an effective amount of the recombinant FVIII polypeptide of claim 1.

13. The method of claim 12, wherein the patient suffers from mild or severe, internal or external, bleeding.

14. The method of claim 12, wherein said disease is hemophilia A.

15. A method for enhancing or restoring blood coagulation in a patient suffering from a coagulation disease, comprising administering to the patient an effective amount of the synthetic blood of claim 11.

16. The method of claim 15, wherein the patient suffers from mild or severe, internal or external, bleeding.

17. The method of claim 15, wherein said disease is hemophilia A.

\* \* \* \* \*